(12) United States Patent
Tommassen et al.

(10) Patent No.: US 8,048,433 B2
(45) Date of Patent: Nov. 1, 2011

(54) DEACYLATION OF LPS IN GRAM NEGATIVE BACTERIA

(75) Inventors: Johannes Petrus Maria Tommassen, Utrecht (NL); Peter André Van Der Ley, Utrecht (NL); Jeroen Johannes Gerardus Geurtsen, Vleuten (NL)

(73) Assignee: NVI Nederlands Vaccininstituut, Bilthoven (NL)

( * ) Notice: Subject to any disclaimer, the term of this patent is extended or adjusted under 35 U.S.C. 154(b) by 470 days.

(21) Appl. No.: 11/722,034

(22) PCT Filed: Dec. 16, 2005

(86) PCT No.: PCT/NL2005/050081
§ 371 (c)(1),
(2), (4) Date: Jun. 10, 2008

(87) PCT Pub. No.: WO2006/065139
PCT Pub. Date: Jun. 22, 2006

(65) Prior Publication Data
US 2008/0274145 A1    Nov. 6, 2008

(30) Foreign Application Priority Data
Dec. 17, 2004 (EP) .................................... 04078445

(51) Int. Cl.
| | |
|---|---|
| A61K 39/02 | (2006.01) |
| A61K 39/095 | (2006.01) |
| A61K 39/10 | (2006.01) |
| A01N 63/00 | (2006.01) |
| A01N 65/00 | (2006.01) |
| C12N 15/00 | (2006.01) |
| C07H 21/02 | (2006.01) |

(52) U.S. Cl. ............... 424/234.1; 424/249.1; 424/250.1; 424/253.1; 424/254.1; 424/93.1; 424/93.2; 435/320.1; 435/252.1; 435/252.3; 536/23.1; 536/23.2; 536/23.7

(58) Field of Classification Search .................. None
See application file for complete search history.

(56) References Cited

U.S. PATENT DOCUMENTS

| | | | | |
|---|---|---|---|---|
| 5,885,586 | A * | 3/1999 | Eckhardt et al. ........... | 424/240.1 |
| 5,939,064 | A * | 8/1999 | Savelkoul et al. .......... | 424/93.2 |
| 2001/0009666 | A1 | 7/2001 | Vose et al. | |

FOREIGN PATENT DOCUMENTS

| | | |
|---|---|---|
| CH | 650 681 A5 | 8/1985 |
| EP | 0 941 738 A1 | 9/1999 |
| WO | 97/19688 A1 | 6/1997 |
| WO | WO 020/85295 A2 * | 10/2002 |

OTHER PUBLICATIONS

Burgess et al (J. of Cell Bio. 111:2129-2138, 1990.*
Bowie et al. Science, 1990, 247:1306-1310.*
Lazar et al. Molecular and Cellular Biology, Mar. 1988, p. 1247-1252.*
Berstad et al. J. Med. Microbiol-vol. 49 (2000), 157-163.*
International Search Report mailed Jul. 4, 2006.
J. Parkhill et al., "Comparative analysis of the genome sequences of *Bordetella pertussis, Bordetella parapertussis* and *Bordetella bronchiseptica*", Nature Genetics, vol. 35, No. 1, pp. 32-40, Sep. 2003.
M. Caroff et al., "Structural variability and originality of the *Bordetella endotoxins*", Journal of Endotoxin Research, vol. 7, No. 1, pp. 63-68, 2001.
M. S. Trent et al., "A PhoP/PhoQ-induced Lipase (PagL) That Catalyzes 3-O-Deacylation of Lipid A Precursors in Membranes of *Salmonella typhimurium*", Journal of Biological Chemistry, vol. 276, No. 12, pp. 9083-9092, Mar. 23, 2001.
M. P. Bos et al., "Identification of an outer membrane protein required for the transport of lipopolysaccharide to the bacterial cell surface", Proceedings of the National Academy of Sciences of the United States of America, vol. 101, No. 25, pp. 9417-9422, Jun. 22, 2004.
C. R. H. Raetz et al. "Lipopolysaccharide Endotoxins", Annual Review of Biochemistry, vol. 71, pp. 635-700, 2002.
J. Geurtsen et al., "Dissemination of Lipid A Deacylases (PagL) among Gram-negative Bacteria", Journal of Biological Chemistry, vol. 280, No. 9, pp. 8248-8259, Mar. 4, 2005.

* cited by examiner

*Primary Examiner* — Oluwatosin Ogunbiyi
(74) *Attorney, Agent, or Firm* — Browdy and Neimark, PLLC

(57) ABSTRACT

The current invention provides new Gram negative polypeptides exhibiting lipid A 3-O-deacylase activity and are capable of modifying and/or detoxifying gram negative LPS. The present invention also provides Gram negative bacteria, Gram negative bacterial lipopolysaccharides (LPS) and compositions comprising LPS, which are provided with or treated with a 3-O-deacylase activity according to the invention and which may be used for pharmaceutical and/or veterinary purposes, in particular for the preparation of whole cell or acellular vaccines against pathogenic Gram negatives such as *Bordetella pertussis, Bordetella parapertussis* and *Bordetella bronchiseptica*.

32 Claims, 14 Drawing Sheets

Fig 2

Figure 1A:
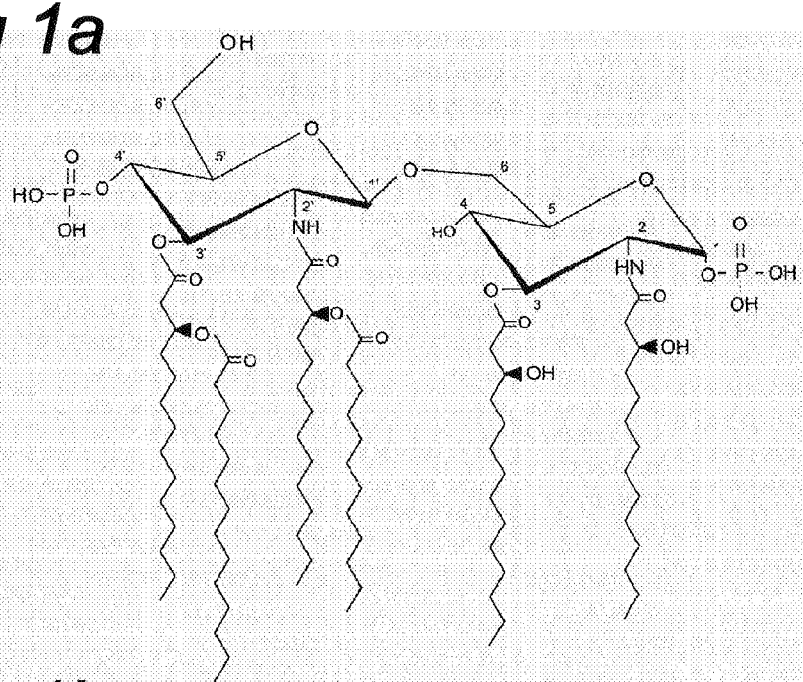

```
S.typhimurium       1  ---------------MYMKRIFIYLLLPCAFACSANDNVFFGK--------CNKHQISFA      37
B.bronchiseptica    1  -----------------MQFLKKNKPLFGIVTLALACATAQAQ---------PTQGGVSLH    35
B.parapertussis     1  -----------------MQFLKKNKPLFGIVTLALACATAQAQ---------PTQGGVSLH    35
B.pertussis         1  -----------------MQFLKKNKPLFGIVTLALACATAQAQ---------PTQGGVSLH    35
P.aeruginosa        1  ------------------MK-KLLPLAVLAALSSVHVASAQAA---------DVSAAVG-A    32
P.fluorescens       1  ------------------MK-RLFCLAAIAAALMGQSFTAQAA---------GVEFAVG-A    32
P.putida            1  ------------------MKTRLAASLAVAVLAFAGADLVQAA---------QISGAVG-A    33
P.syringae          1  ------------------MK-RLFCLAVIAAALAGQASIAQAD---------GVEFSVG-Q    32
B.fungorum          1  ------------MNNKKNVLRDLALKITAGAV-LVGASGVASAD------QFGVQVAGG-L    41
B.mallei            1  ------------MNDKNGGRVGRAIARTALALALVCASCSAFAD------RWGLQLGGG-V    42
B.pseudomallei      1  ------------MNDKNGGRVGRAIARTALALALVCASCSAFAD------RWGLQLGGG-V    42
R.metallidurans     1  ------------MPPANLSRKLPSARLLAIAAIVAGASSAASAE ELVGWAHPAVQAAFABD    49
R.solanacearum      1  ------------MTRSALPR---SAKLLAAAVSAAPTLAAAPAQ-----ADPSVRAIYGRD    41
A.vinelandii        1  -----------------MR-KYLSLPAVAVLLLGSAGVAQAV--------EVGAAVG-V    32

S.typhimurium      38  AGESIRRGGVEHLYTAFLTYSEPSD----FFFLQAPNELELGGFKAK-GSDDCSKHSGSV    92
B.bronchiseptica   36  YGIGDHYQRVTLNYETPTLWSHQFGGNWGRLDLTPELGASYWWADGS-RSPGHVWQASAI    94
B.parapertussis    36  YGIGDHYQRVTLNYETPTLWSHQFGGNWGRLDLTPELGASYWWADGS-RSPGHVWQASAI    94
B.pertussis        36  YGIGDHYQRVTLNYETPTLWSHQFGGNWGPLDLTPELGASYWWADGS-RSPGHVWQASAI    94
P.aeruginosa       33  TSQSGMTYRLGLSWDWDKSWWQTST---GRLTGYWDAGYTYWEGG---DEGAGKHSLSFA    86
P.fluorescens      33  TSDSTMTYRLGMNFDWDKSWLQSDV---GRLTGYWSGAYTYWEGD---KTSSPNSLSFS    85
P.putida           34  TGQGDMTYPLGMSFDWDRKWLESST---GHVSGYWDAATYWEGG---DASGAHSLSFS    86
P.syringae         33  TGESTMTYRLGVQFDWDKTWLQSDI---GRLTGYWDGAYTYWDGK---DYKDHSLSFS    85
B.fungorum         42  GDFHVKKLDLGFVWDPDLNWWQICD--WRFSLIGEAHVAWN-HTREQNVEDRIGEVGVT    97
B.mallei           43  ADHDMKKGDTAVVWDPNWTWWEIGG---WHFAFVAEGHLSYWRYTGDRAINSSTWEVGAT    99
B.pseudomallei     43  ADHLMKKGDIAVVWDPNWTWWEIGG---WHFAFVAEGHLSYWRYTGDRAINSSTWEVGAT    99
R.metallidurans    50  TDHGINKYEIAVHFWTPIQYGNPXG---WLFRLQAEANWGYW-DARSGTNRQNLMEFGLT    105
R.solanacearum     42  NRHGIEKYGVOIDFDSGFHCGNPQG---WFLNLDWEIALGQW-RSTFGTNRQNLTEFGVT    97
A.vinelandii       33  TSQNDWTYRLSLGLFNERQWWKSDL---GIVTGYWDAGYTYWEGGSGNDKYAGAHSLSFS    89

S.typhimurium      93  PCNKYNQGVLGISKDVALVHSAGIYTGIGLGAYIKSKSRDDMRVNSAFTFGEKAFLGWNF    152
B.bronchiseptica   95  PMFRWWTG--------ERFY--IEAGIGATVFSSTSFADKR-IGSAFQFGDHIGLGFLL    142
B.parapertussis    95  PMFRWWTG--------ERFY--IEAGIGATVFSSTSFADKR-IGSAFQFGDHIGLGFLL    142
B.pertussis        95  PMFRWWTG--------ERFY--IEAGIGATVFSSTSFADKR-IGSAFQFGDHIGLGFLL    142
P.aeruginosa       87  PVFVYEFAG-DS-----IRPF--IEAGIGVAAFSGTRVGDQR-LGSSLNFEDRIGACLRF    137
P.fluorescens      86  PVFVYEFAG-QS-----VKPY--VEACIGVALFSNTEYEDNK-LGGSFQFEDRLGFGLRF    136
P.putida           87  PVFTXEFSG-FT-----XTPY--IEAGIGLAAFSKEDVGDQR-LGSAVNFEDRIGFGLRL    137
P.syringae         86  PVLVYEFGN-GN-----VKPY--LEAGIGVSVFSNTQVEDRK-FGSAENFEDRIGFGLRF    136
B.fungorum         98  PIIRFIKES-GF-----IRPY--AELGAGIRLLSSPRISSTFTLGTAFQFADMAGVGMQF    149
B.mallei          100  PIIRFIKSA-GY-----VRPF--VELGAGVRFLSHPTISQNYSMSTSFQFADMVGVGAQF    151
B.pseudomallei    100  PIIRFIKSA-GY-----VRPF--VELCACVRFLSHPTISQNYSMSTSFQFADMVGVGAQF    151
R.metallidurans   106  PILRVEKRG-GY-----FVPF--LEAGVGLEILTHTSTSDQHNFSTAFQFGDMVGLGVGF    157
R.solanacearum     98  PLFRLEKRG-GS-----WVPF--IEAGIGPRLLSHTPTSDEHNESTAFQFSDMIGVGVAE    149
A.vinelandii       90  PVFTYEFSGFSS-----VTPF--LELGVGVAFFSKTRVGEQQ-LGSSFNFEDRIGAGIKF    141

S.typhimurium     153  GAFS---TEAYIRHFSNGSLTDKNSGRNFVGASISYNF    187
B.bronchiseptica  143  TPSN--RIGLRYSHFSNAGIKEPNPGLDIVQLTYTYQF    178
B.parapertussis   143  TPSN--RIGLRYSHFSNAGIKEPNPGLDIVQLTYTYQF    178
B.pertussis       143  TPSN--RIGLRYSHFSNAGIKEPNPGLDIYQLTYTYQF    178
P.aeruginosa      138  ANGQ--SVGVRAIHYSNAGLKQPNDGIESYSLFYKIFI    173
P.fluorescens     137  NGGH--EVGIRATHYSNAGLSSDRDGVESYSLRYTMPL    172
P.putida          138  PGEQ--RVGIRAMHYSNAGIKQPNDGIESYSLFYSTAF    173
P.syringae        137  AGGR--EVGIRATHYSNAGIKEPNDGIESYALRYKMPF    172
B.fungorum        150  GNRQQYQAGYRFQHISNAGIKEPNPGINFHQLYLQYNF    187
B.mallei          152  GNHQQYQAGFRFQHVSNAGIKDPNPGINFSQLYVQYNF    189
B.pseudomallei    152  GNRQQYQAGFRFQHVSNAGIKDFNPCINFSQLYVQYNF    189
R.metallidurans   158  GKNAATEVGMRFQHISNAGIKEPNPGTNLYTGYVRYRF    195
R.solanacearum    150  GSRQQFQVGYRFEHLSNASIKRPNPGTDLNELYLRYTF    187
A.vinelandii      142  AGGQ--RVGIRAIHYSNAGIKQPNDGIESFSAYYSHAF    177
```

Tohama WT    Tohama PagL

Cell envelopes — No membranes, PagL(Bb), PagL(Pa), PagL(St), pET-11a

Refolded — No PagL, 4 ug PagL, 4 ug PagL +EDTA

SEQUENCE LISTING

```
<160> NUMBER OF SEQ ID NOS: 40

<210> SEQ ID NO 1
<211> LENGTH: 178
<212> TYPE: PRT
<213> ORGANISM: Bordetella sp.

<400> SEQUENCE: 1

Met Gln Phe Leu Lys Lys Asn Lys Pro Leu Phe Gly Ile Val Thr Leu
1               5                   10                  15

Ala Leu Ala Cys Ala Thr Ala Gln Ala Gln Pro Thr Gln Gly Gly Val
            20                  25                  30

Ser Leu His Tyr Gly Ile Gly Asp His Tyr Gln Arg Val Thr Leu Asn
        35                  40                  45

Tyr Glu Thr Pro Thr Leu Trp Ser His Gln Phe Gly Gly Asn Trp Gly
    50                  55                  60

Arg Leu Asp Leu Thr Pro Glu Leu Gly Ala Ser Tyr Trp Trp Ala Asp
65                  70                  75                  80

Gly Ser Arg Ser Pro Gly His Val Trp Gln Ala Ser Ala Ile Pro Met
                85                  90                  95

Phe Arg Trp Trp Thr Gly Glu Arg Phe Tyr Ile Glu Ala Gly Ile Gly
            100                 105                 110
```

```
Ala Thr Val Phe Ser Ser Thr Ser Phe Ala Asp Lys Arg Ile Gly Ser
        115                 120                 125

Ala Phe Gln Phe Gly Asp His Ile Gly Leu Gly Phe Leu Leu Thr Pro
    130                 135                 140

Ser Asn Arg Ile Gly Leu Arg Tyr Ser His Phe Ser Asn Ala Gly Ile
145                 150                 155                 160

Lys Glu Pro Asn Pro Gly Leu Asp Ile Val Gln Leu Thr Tyr Thr Tyr
                165                 170                 175

Gln Phe

<210> SEQ ID NO 2
<211> LENGTH: 537
<212> TYPE: DNA
<213> ORGANISM: Bordetella bronchiseptica

<400> SEQUENCE: 2
atgcaatttc tcaagaaaaa caagcccctg ttcggcatcg ttacactggc tctggcatgt      60
gccaccgccc aggcgcagcc cactcagggc ggggtcagcc tgcattacgg tattggcgac     120
cactatcagc gcgtcacgct gaactacgaa acccccacgc tctggagcca ccagttcggc     180
ggcaattggg gccgcctgga cctgaccccc gaactgggcg cgtcatactg gtgggccgac     240
ggctcgcgct cgcccggcca cgtgtggcag gccagcgcca ttccgatgtt ccgctggtgg     300
accggcgagc gcttttacat cgaggccggc atcgcgcca cggttttcag cagcaccagc     360
ttcgccgaca gcgcatcgg ttcggccttc cagtttggcg accatatcgg ctgggcttc      420 ctgctgacgc ccagcaaccg catcggcctg cgctattcgc acttctccaa cgccggcatc     480
aaggaaccga accccggcct cgatatcgtg cagctgacct atacgtacca gttctga        537

<210> SEQ ID NO 3
<211> LENGTH: 537
<212> TYPE: DNA
<213> ORGANISM: Bordetella parapertussis

<400> SEQUENCE: 3
atgcaatttc tcaagaaaaa caagcccctg ttcggcatcg ttacactggc tctggcatgt      60
gccaccgccc aggcgcagcc cactcagggc ggggtcagcc tgcactacgg tattggcgac     120
cactatcagc gcgtcacgct gaactacgaa acccccacgc tctggagcca ccagttcggc     180
ggcaattggg gccgcctgga cctgaccccc gaactgggcg cgtcgtactg gtgggccgac     240
ggctcgcgct cgcccggcca cgtgtggcag gccagcgcca ttccgatgtt ccgctggtgg     300
accggcgagc gcttctacat cgaggccggc atcgcgcca cggttttcag cagcaccagc     360
ttcgccgaca gcgcatcgg ttcggccttc cagtttggcg accatatcgg ctgggcttc      420 ctgctgacgc ccagcaaccg catcggcctg cgctattcgc acttctccaa cgccggcatc     480
aaggaaccga accccggcct cgatatcgtg cagctgacct atacgtacca gttctga        537

<210> SEQ ID NO 4
<211> LENGTH: 535
<212> TYPE: DNA
<213> ORGANISM: Bordetella pertussis

<400> SEQUENCE: 4
atgcaatttc tcaagaaaaa caagcccctg ttcggcatcg ttacactggc cctggcatgt      60
gccaccgccc aggcgcagcc cactcagggc ggggtgcctg cattacggta ttggcgacca     120
ctatcagcgc gtcacgctga actacgaaac tcccacgctc tggagccacc agttcggcgg     180
```

-continued

```
aaattggggc cgcctggacc tgaccccga actgggcgcg tcgtactggt gggccgacgg    240
ctcgcgctcg cccggccacg tgtggcaggc cagcgccatt ccgatgttcc gctggtggac    300
cggcgagcgc ttctacatcg aggccggcat cggcgccacg gttttcagca gcaccagctt    360
cgccgacaag cgcatcggtt cggccttcca gtttggcgac catatcggac tgggcttcct    420
gctgacgccc agcaatcgta tcggcctgcg ctattcgcat ttctcgaacg ccggcatcaa    480
ggaaccgaac cccggcctgg atatcgtgca gctgacctat acgtaccagt ctga          535
```

<210> SEQ ID NO 5
<211> LENGTH: 537
<212> TYPE: DNA
<213> ORGANISM: Bordetella pertussis
<220> FEATURE:
<222> LOCATION: (96)..(97)
<223> OTHER INFORMATION: Frameshift restored

<400> SEQUENCE: 5

```
atgcaatttc tcaagaaaaa caagcccctg ttcggcatcg ttacactggc cctggcatgt     60
gccaccgccc aggcgcagcc cactcagggc ggggtcagcc tgcattacgg tattggcgac    120
cactatcagc gcgtcacgct gaactacgaa actcccacgc tctggagcca ccagttcggc    180
ggaaattggg gccgcctgga cctgaccccc gaactgggcg cgtcgtactg gtgggccgac    240
ggctcgcgct cgcccggcca cgtgtggcag gccagcgcca ttccgatgtt ccgctggtgg    300
accggcgagc gcttctacat cgaggccggc atcggcgcca cggttttcag cagcaccagc    360
ttcgccgaca agcgcatcgg ttcggccttc cagtttggcg accatatcgg actgggcttc    420
ctgctgacgc ccagcaatcg tatcggcctg cgctattcgc atttctcgaa cgccggcatc    480
aaggaaccga accccggcct ggatatcgtg cagctgacct atacgtacca gttctga       537
```

<210> SEQ ID NO 6
<211> LENGTH: 173
<212> TYPE: PRT
<213> ORGANISM: Pseudomonas aeruginosa

<400> SEQUENCE: 6

```
Met Lys Lys Leu Leu Pro Leu Ala Val Leu Ala Ala Leu Ser Ser Val
1               5                   10                  15

His Val Ala Ser Ala Gln Ala Ala Asp Val Ser Ala Ala Val Gly Ala
            20                  25                  30

Thr Gly Gln Ser Gly Met Thr Tyr Arg Leu Gly Leu Ser Trp Asp Trp
        35                  40                  45

Asp Lys Ser Trp Trp Gln Thr Ser Thr Gly Arg Leu Thr Gly Tyr Trp
    50                  55                  60

Asp Ala Gly Tyr Thr Tyr Trp Glu Gly Gly Asp Glu Gly Ala Gly Lys
65                  70                  75                  80

His Ser Leu Ser Phe Ala Pro Val Phe Val Tyr Glu Phe Ala Gly Asp
                85                  90                  95

Ser Ile Lys Pro Phe Ile Glu Ala Gly Ile Gly Val Ala Ala Phe Ser
            100                 105                 110

Gly Thr Arg Val Gly Asp Gln Asn Leu Gly Ser Ser Leu Asn Phe Glu
        115                 120                 125

Asp Arg Ile Gly Ala Gly Leu Lys Phe Ala Asn Gly Gln Ser Val Gly
    130                 135                 140

Val Arg Ala Ile His Tyr Ser Asn Ala Gly Leu Lys Gln Pro Asn Asp
145                 150                 155                 160

Gly Ile Glu Ser Tyr Ser Leu Phe Tyr Lys Ile Pro Ile
```

```
                165                 170

<210> SEQ ID NO 7
<211> LENGTH: 172
<212> TYPE: PRT
<213> ORGANISM: Pseudomonas fluorescens

<400> SEQUENCE: 7

Val Lys Arg Leu Phe Cys Leu Ala Ala Ile Ala Ala Leu Met Gly
1               5                   10                  15

Gln Ser Phe Thr Ala Gln Ala Ala Gly Val Glu Phe Ala Val Gly Ala
                20                  25                  30

Thr Ser Asp Ser Thr Met Thr Tyr Arg Leu Gly Met Asn Phe Asp Trp
            35                  40                  45

Asp Lys Ser Trp Leu Gln Ser Asp Val Gly Arg Leu Thr Gly Tyr Trp
    50                  55                  60

Ser Gly Ala Tyr Thr Tyr Trp Glu Gly Asp Lys Thr Ser Ser Asn Asn
65                  70                  75                  80

Ser Leu Ser Phe Ser Pro Val Phe Val Tyr Glu Phe Ala Gly Gln Ser
                85                  90                  95

Val Lys Pro Tyr Val Glu Ala Gly Ile Gly Val Ala Leu Phe Ser Asn
            100                 105                 110

Thr Glu Tyr Glu Asp Asn Lys Leu Gly Gly Ser Phe Gln Phe Glu Asp
        115                 120                 125

Arg Leu Gly Phe Gly Leu Arg Phe Asn Gly Gly His Glu Val Gly Ile
    130                 135                 140

Arg Ala Thr His Tyr Ser Asn Ala Gly Leu Ser Ser Asp Asn Asp Gly
145                 150                 155                 160

Val Glu Ser Tyr Ser Leu His Tyr Thr Met Pro Leu
                165                 170

<210> SEQ ID NO 8
<211> LENGTH: 172
<212> TYPE: PRT
<213> ORGANISM: Pseudomonas syringae

<400> SEQUENCE: 8

Met Lys Arg Leu Phe Cys Leu Ala Val Ile Ala Ala Leu Ala Gly
1               5                   10                  15

Gln Ser Ala Ile Ala Gln Ala Asp Gly Val Glu Phe Ser Val Gly Gln
                20                  25                  30

Thr Gly Glu Ser Thr Met Thr Tyr Arg Leu Gly Val Gln Phe Asp Trp
            35                  40                  45

Asp Lys Thr Trp Leu Gln Ser Asp Ile Gly Arg Leu Thr Gly Tyr Trp
    50                  55                  60

Asp Gly Ala Tyr Thr Tyr Trp Asp Gly Lys Asp Tyr Lys Asp Asn His
65                  70                  75                  80

Ser Leu Ser Phe Ser Pro Val Leu Val Tyr Glu Phe Gly Asn Gly Asn
                85                  90                  95

Val Lys Pro Tyr Leu Glu Ala Gly Ile Gly Val Ser Val Phe Ser Asn
            100                 105                 110

Thr Gln Val Glu Asp Arg Lys Phe Gly Ser Ala Phe Asn Phe Glu Asp
        115                 120                 125

Arg Ile Gly Phe Gly Leu Arg Phe Ala Gly Gly His Glu Val Gly Ile
    130                 135                 140

Arg Ala Thr His Tyr Ser Asn Ala Gly Ile Lys Glu Pro Asn Asp Gly
145                 150                 155                 160
```

Ile Glu Ser Tyr Ala Leu His Tyr Lys Met Pro Phe
            165                 170

<210> SEQ ID NO 9
<211> LENGTH: 173
<212> TYPE: PRT
<213> ORGANISM: Pseudomonas putida

<400> SEQUENCE: 9

Met Lys Thr Arg Leu Ala Ala Ser Leu Ala Val Ala Val Leu Ala Phe
1               5                   10                  15

Ala Gly Ala Asp Leu Val Gln Ala Gln Ile Ser Gly Ala Val Gly
            20                  25                  30

Ala Thr Gly Gln Gly Asp Met Thr Tyr Arg Ile Gly Met Ser Phe Asp
            35                  40                  45

Trp Asp Lys Lys Trp Leu Glu Ser Ser Thr Gly His Val Ser Gly Tyr
50                  55                  60

Trp Asp Ala Ala Tyr Thr Tyr Trp Glu Gly Asp Ala Ser Gly Ala
65                  70                  75                  80

His Ser Leu Ser Phe Ser Pro Val Phe Thr Tyr Glu Phe Ser Gly Phe
                85                  90                  95

Thr Tyr Thr Pro Tyr Ile Glu Ala Gly Ile Gly Leu Ala Ala Phe Ser
            100                 105                 110

Lys Thr Asp Val Gly Asp Gln Arg Leu Gly Ser Ala Val Asn Phe Glu
        115                 120                 125

Asp Arg Ile Gly Phe Gly Leu Lys Leu Pro Gly Glu Gln Lys Val Gly
130                 135                 140

Ile Arg Ala Met His Tyr Ser Asn Ala Gly Ile Lys Gln Pro Asn Asp
145                 150                 155                 160

Gly Ile Glu Ser Tyr Ser Leu Phe Tyr Ser Thr Ala Phe
                165                 170

<210> SEQ ID NO 10
<211> LENGTH: 172
<212> TYPE: PRT
<213> ORGANISM: Pseudomonas putida

<400> SEQUENCE: 10

Met Arg Lys Leu Leu Gly Leu Ala Ala Ala Ala Phe Val Leu Gly
1               5                   10                  15

Gln Ala Met Ser Ala Gln Ala Asp Val Ser Phe Ser Val Gly Gln
            20                  25                  30

Thr Gly Asp Ser Thr Met Val Tyr Arg Leu Gly Leu Gln Ser Asn Trp
            35                  40                  45

Asp Ala Ser Trp Trp Gln Thr Ser Val Gly Arg Leu Thr Gly Tyr Trp
50                  55                  60

Asp Gly Ala Tyr Thr Tyr Trp Asp Gly Asp Thr Ala Ser Asn His
65                  70                  75                  80

Ser Leu Ser Phe Ala Pro Val Phe Val Tyr Glu Phe Ala Gly Glu Ser
                85                  90                  95

Val Lys Pro Tyr Ile Glu Ala Gly Ile Gly Val Ala Ala Phe Ser Ser
            100                 105                 110

Thr Glu Leu Glu Ser Asn Glu Leu Gly Ser Ala Phe Gln Phe Glu Asp
        115                 120                 125

Arg Ile Gly Phe Gly Leu Arg Phe Ala Gly Gly His Glu Ile Gly Val
130                 135                 140

```
Arg Ala Ile His Tyr Ser Asn Ala Gly Ile Lys Glu Pro Asn Asp Gly
145                 150                 155                 160

Val Glu Ser Tyr Ser Leu His Tyr Arg Met Ala Leu
                165                 170
```

<210> SEQ ID NO 11
<211> LENGTH: 187
<212> TYPE: PRT
<213> ORGANISM: Burkholderia fungorum

<400> SEQUENCE: 11

```
Met Asn Lys Lys Asn Val Leu Arg Asp Leu Ala Leu Lys Ile Thr
1               5                   10                  15

Ala Gly Ala Val Leu Val Gly Ala Ser Gly Val Ala Ser Ala Asp Gln
                20                  25                  30

Phe Gly Val Gln Val Ala Gly Leu Gly Asp Arg His Val Lys Lys
        35                  40                  45

Leu Asp Leu Gly Phe Val Trp Asp Pro Asp Leu Asn Trp Trp Gln Ile
50                  55                  60

Gly Asp Trp His Phe Ser Leu Ile Gly Glu Ala His Val Ala Trp Trp
65                  70                  75                  80

His Thr Asn Glu Gly Asn Val His Asp Asn Ile Gly Glu Val Gly Val
                85                  90                  95

Thr Pro Ile Ile Arg Phe Ile Lys Glu Ser Gly Pro Ile Arg Pro Tyr
                100                 105                 110

Ala Glu Leu Gly Ala Gly Ile Arg Leu Leu Ser Ser Pro Arg Ile Ser
            115                 120                 125

Ser Thr Phe Thr Leu Gly Thr Ala Phe Gln Phe Ala Asp Met Ala Gly
        130                 135                 140

Val Gly Met Gln Phe Gly Asn Arg Gln Gln Tyr Gln Ala Gly Tyr Arg
145                 150                 155                 160

Phe Gln His Ile Ser Asn Gly Gly Ile Lys Glu Pro Asn Pro Gly Ile
                165                 170                 175

Asn Phe His Gln Leu Tyr Leu Gln Tyr Asn Phe
                180                 185
```

<210> SEQ ID NO 12
<211> LENGTH: 189
<212> TYPE: PRT
<213> ORGANISM: Burkholderia mallei

<400> SEQUENCE: 12

```
Met Asn Asp Lys Asn Gly Gly Arg Val Gly Arg Ala Ile Ala Arg Thr
1               5                   10                  15

Ala Leu Ala Leu Ala Leu Val Gly Ala Ser Gly Ser Ala Phe Ala Asp
                20                  25                  30

Arg Trp Gly Leu Gln Leu Gly Gly Val Ala Asp His Asp Met Lys
        35                  40                  45

Lys Gly Asp Ile Ala Val Val Trp Asp Pro Asn Trp Thr Trp Trp Glu
50                  55                  60

Ile Gly Gly Trp His Phe Ala Phe Val Ala Glu Gly His Leu Ser Tyr
65                  70                  75                  80

Trp Arg Tyr Thr Gly Asp Arg Ala Ile Asn Ser Ser Ile Trp Glu Val
                85                  90                  95

Gly Ala Thr Pro Ile Ile Arg Phe Ile Lys Ser Ala Gly Tyr Val Arg
                100                 105                 110

Pro Phe Val Glu Leu Gly Ala Gly Val Arg Phe Leu Ser His Pro Thr
```

```
            115                 120                 125
Ile Ser Gln Asn Tyr Ser Met Ser Thr Ser Phe Gln Phe Ala Asp Met
        130                 135                 140

Val Gly Val Gly Ala Gln Phe Gly Asn His Gln Gln Tyr Gln Ala Gly
145                 150                 155                 160

Phe Arg Phe Gln His Val Ser Asn Ala Gly Ile Lys Asp Pro Asn Pro
                165                 170                 175

Gly Ile Asn Phe Ser Gln Leu Tyr Val Gln Tyr Asn Phe
            180                 185

<210> SEQ ID NO 13
<211> LENGTH: 189
<212> TYPE: PRT
<213> ORGANISM: Burkholderia pseudomallei

<400> SEQUENCE: 13

Met Asn Asp Lys Asn Gly Gly Arg Val Gly Arg Ala Ile Ala Ar

Ala Gly Ala His Ser Leu Ser Phe Ser Pro Val Phe Thr Tyr Glu Phe
            85                  90                  95

Ser Gly Phe Ser Ser Val Thr Pro Phe Leu Glu Leu Gly Val Gly Val
            100                 105                 110

Ala Phe Phe Ser Lys Thr Arg Val Gly Glu Gln Leu Gly Ser Ser
            115                 120                 125

Phe Asn Phe Glu Asp Arg Ile Gly Ala Gly Ile Lys Phe Ala Gly Gly
130                 135                 140

Gln Lys Val Gly Ile Arg Ala Ile His Tyr Ser Asn Ala Gly Ile Lys
145                 150                 155                 160

Gln Pro Asn Asp Gly Ile Glu Ser Phe Ser Ala Tyr Tyr Ser His Ala
                165                 170                 175

Phe

<210> SEQ ID NO 15
<211> LENGTH: 195
<212> TYPE: PRT
<213> ORGANISM: Ralstonia metallidurans

<400> SEQUENCE: 15

Met Pro Pro Ala Asn Leu Ser Arg Lys Leu Pro Ser Ala Arg Leu Leu
1               5                   10                  15

Ala Ile Ala Ala Leu Val Ala Gly Ala Ser Ser Ala Ala Ser Ala Glu
            20                  25                  30

Glu Leu Val Gly Trp Ala His Pro Ala Val Gln Ala Ala Phe Ala Arg
        35                  40                  45

Asp Thr Asp His Gly Ile Asn Lys Tyr Glu Ile Ala Val Asn Phe Asn
50                  55                  60

Thr Pro Ile Gln Tyr Gly Asn Pro Asp Gly Trp Leu Phe Arg Leu Gln
65                  70                  75                  80

Ala Glu Ala Asn Met Gly Tyr Trp Asp Ala Arg Ser Gly Thr Asn Arg
                85                  90                  95

Gln Asn Leu Met Glu Phe Gly Leu Thr Pro Ile Leu Arg Val Glu Lys
            100                 105                 110

Arg Gly Gly Tyr Phe Val Pro Phe Leu Glu Ala Gly Val Gly Leu Arg
        115                 120                 125

Leu Leu Thr His Thr Ser Thr Ser Asp Gln His Asn Phe Ser Thr Ala
130                 135                 140

Phe Gln Phe Gly Asp Met Val Gly Leu Gly Val Gly Phe Gly Lys Asn
145                 150                 155                 160

Ala Ala Thr Glu Val Gly Met Arg Phe Gln His Ile Ser Asn Ala Gly
                165                 170                 175

Ile Lys Glu Pro Asn Pro Gly Thr Asn Leu Tyr Thr Gly Tyr Val Arg
            180                 185                 190

Tyr Arg Phe
        195

<210> SEQ ID NO 16
<211> LENGTH: 187
<212> TYPE: PRT
<213> ORGANISM: Ralstonia solanacearum

<400> SEQUENCE: 16

Met Thr Arg Ser Ala Leu Pro Arg Ser Ala Lys Leu Leu Ala Ala Ala
1               5                   10                  15

Val Ser Ala Ala Thr Leu Leu Ala Ala Ala Pro Ala Gln Ala Asp Pro

```
                    20                  25                  30
Ser Val Arg Ala Ile Tyr Gly Arg Asp Asn Arg His Gly Ile Glu Lys
        35                  40                  45
Tyr Gly Val Asp Ile Asp Phe Asp Ser Gly Phe His Cys Gly Asn Pro
    50                  55                  60
Gln Gly Trp Phe Leu Asn Leu Asp Trp Glu Ile Ala Leu Gly Gln Trp
65                  70                  75                  80
Arg Ser Thr Lys Gly Thr Asn Arg Gln Asn Leu Thr Glu Phe Gly Val
                85                  90                  95
Thr Pro Leu Phe Arg Leu Glu Lys Arg Gly Gly Ser Trp Val Pro Phe
            100                 105                 110
Ile Glu Ala Gly Ile Gly Pro Arg Leu Leu Ser His Thr Arg Thr Ser
        115                 120                 125
Asp Glu His Asn Phe Ser Thr Ala Phe Gln Phe Ser Asp Met Ile Gly
    130                 135                 140
Val Gly Val Ala Phe Gly Ser Arg Gln Gln Phe Gln Val Gly Tyr Arg
145                 150                 155                 160
Phe Glu His Leu Ser Asn Ala Ser Ile Lys Arg Pro Asn Pro Gly Thr
                165                 170                 175
Asp Leu Asn Glu Leu Tyr Leu Arg Tyr Thr Phe
            180                 185

<210> SEQ ID NO 17
<211> LENGTH: 187
<212> TYPE: PRT
<213> ORGANISM: Salmonella typhimurium

<400> SEQUENCE: 17

Met Tyr Met Lys Arg Ile Phe Ile Tyr Leu Leu Leu Pro Cys Ala Phe
1               5                   10                  15
Ala Cys Ser Ala Asn Asp Asn Val Phe Phe Gly Lys Gly Asn Lys His
                20                  25                  30
Gln Ile Ser Phe Ala Ala Gly Glu Ser Ile Arg Arg Gly Gly Val Glu
        35                  40                  45
His Leu Tyr Thr Ala Phe Leu Thr Tyr Ser Glu Pro Ser Asp Phe Phe
    50                  55                  60
Phe Leu Gln Ala Arg Asn Asn Leu Glu Leu Gly Gly Phe Lys Ala Lys
65                  70                  75                  80
Gly Ser Asp Asp Cys Ser Lys His Ser Gly Ser Val Pro Cys Asn Lys
                85                  90                  95
Tyr Asn Gln Gly Val Leu Gly Ile Ser Lys Asp Val Ala Leu Val His
            100                 105                 110
Phe Ala Gly Ile Tyr Thr Gly Ile Gly Leu Gly Ala Tyr Ile Lys Ser
        115                 120                 125
Lys Ser Arg Asp Asp Met Arg Val Asn Ser Ala Phe Thr Phe Gly Glu
    130                 135                 140
Lys Ala Phe Leu Gly Trp Asn Phe Gly Ala Phe Ser Thr Glu Ala Tyr
145                 150                 155                 160
Ile Arg His Phe Ser Asn Gly Ser Leu Thr Asp Lys Asn Ser Gly His
                165                 170                 175
Asn Phe Val Gly Ala Ser Ile Ser Tyr Asn Phe
            180                 185

<210> SEQ ID NO 18
<211> LENGTH: 27
<212> TYPE: DNA
```

```
<213> ORGANISM: Unknown
<220> FEATURE:
<223> OTHER INFORMATION: chemically synthesized oligonucleotide primer

<400> SEQUENCE: 18
aacatatgaa gagaatattt atatatc                                         27

<210> SEQ ID NO 19
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 19
aacatatgaa gaaactactt ccgctgg                                         27

<210> SEQ ID NO 20
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 2
aacatatggc ggacgtctcg gccgccg                                         27

<210> SEQ ID NO 21
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 21
aacatatgca atttctcaag aaaaaca                                         27

<210> SEQ ID NO 22
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 22
aaggatcctc agaaattata actaatt                                         27

<210> SEQ ID NO 23
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 23
aaggatccct agatcgggat cttgtag                                         27

<210> SEQ ID NO 24
<211> LENGTH: 27
<212> TYPE: DNA
<213> ORGANISM: Unknown
<220> FEATURE:
<223> OTHER INFORMATION: chemically synthesized oligonucleotide primer

<400> SEQUENCE: 24
aaggatcctc agaactggta cgtatag                                         27
```

-continued

<210> SEQ ID NO 25
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 25
gaaggcgccg gcaaggcgtc gctgtcgttc gct         33

<210> SEQ ID NO 26
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 32
agcgaacgac agcgacgcct tgccggcgcc ttc         33

<210> SEQ ID NO 27
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 27
gaaggcgccg gcaagaactc gctgtcgttc gct         33

<210> SEQ ID NO 28
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 28
agcgaacgac agcgagttct tgccggcgcc ttc         33

<210> SEQ ID NO 29
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 29
ggcaagcatt cgctggcgtt cgctccggta ttc         33

<210> SEQ ID NO 30
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 30
gaataccgga gcgaacgcca gcgaatgctt gcc         33

<210> SEQ ID NO 31
<211> LENGTH: 33
<212> TYPE: DNA
<213> ORGANISM: Unknown
<220> FEATURE:
<223> OTHER INFORMATION: chemically synthesized oligonucleotide primer

```
<210> SEQ ID NO 31
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 31 ggcaagcattcgctgtgcttcgctccggtattc                                    33

<210> SEQ ID NO 32
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 32
gaataccgga gcgaagcaca gcgaatgctt gcc                                 33

<210> SEQ ID NO 33
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 33
ggcgttcggg cgatcgcgta ttccaacgcc ggc                                 33

<210> SEQ ID NO 34
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 34
gccggcgttg gaatacgcga tcgcccgaac gcc                                 33

<210> SEQ ID NO 35
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 35
ggcgttcggg cgatcaacta ttccaacgcc ggc                                 33

<210> SEQ ID NO 36
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 36
gccggcgttg gaatagttga tcgcccgaac gcc                                 33

<210> SEQ ID NO 37
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 37
cgggcgatcc actatgcgaa cgccggcctg aaa                                 33

<210> SEQ ID NO 38
<211> LENGTH: 33
<212> TYPE: DNA
```

```
<213> ORGANISM: Unknown
<220> FEATURE:
<223> OTHER INFORMATION: chemically synthesized oligonucleotide primer

<400> SEQUENCE: 38
tttcaggccg gcgttcgcat agtggatcgc ccg                          33

<210> SEQ ID NO 39
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 39
cgggcgatcc actattgcaa cgccggcctg aaa                          33

<210> SEQ ID NO 40
<211> LENGTH: 33
<212> TYPE: DNA
<213> ORGANISM: Unknown
<220> FEATURE:
<223> OTHER INFORMATION: chemically synthesized oligonucleotide primer

<400> SEQUENCE: 40
tttcaggccg gcgttgcaat agtggatcgc ccg                          33
```

DEACYLATION OF LPS IN GRAM NEGATIVE BACTERIA

This application is the U.S. National Stage of International Application No. PCT/NL05/50081, filed Dec. 16, 2005, and claims priority under 35 U.S.C §119 to European Patent Office (EPO) 04078445.6 Dec. 17, 2004.

FIELD OF THE INVENTION

The current invention relates to the field of microbiology, in particular the biology of Gram negative LPS synthesis and modification. The invention also relates to the field of medicine, in particular to the field of vaccination against bacterial pathogens. The present invention further relates to Gram negative bacteria, Gram negative bacterial lipopolysaccharides (LPS) and compositions comprising LPS, which may be used for pharmaceutical and/or veterinary purposes, in particular for the preparation of vaccines against Gram negatives such as *Bordetella pertussis, Bordetella parapertussis* and *Bordetella bronchiseptica*. The invention further provides vaccines containing deacylated LPS, and to the use of modified and detoxified LPS in the preparation of whole cell and acellular vaccines.

BACKGROUND OF THE INVENTION

*Bordetella pertussis* infection is causative agent of whooping cough, with an estimated number of 60 millions cases each year, killing approximately 355,000 people worldwide annually (WHO), in particular children and immune compromised individuals. Although treatment with antibiotics is available (erythromycin), by the time the disease is diagnosed, bacterial toxins have often caused severe damage. Prevention of the disease is therefore of great importance. The prime means of control remains vaccination. Conventionally, vaccines against pertussis ("whooping-cough") infections have been based on whole cells of *B. pertussis*. Whole cell *Bordetella pertussis* vaccines, comprising whole bacteria that have been killed by heat treatment, formalin or other means, have been included in general vaccination programs since the early 1950's.

Immunization with the whole-cell pertussis vaccine, while effective at preventing whooping cough in infants, has been associated with local, systemic and neurological reactions, including fevers, convulsions and encephalopathy in children. LPS is responsible for the major part of the adverse reactions in children following pertussis immunization. During bacterial infections of animals, LPS or its lipid A moiety activates the innate immune system through interaction with Toll-like receptors, primarily TLR-4. The host response to lipid A includes the production of cationic antimicrobial peptides, cytokines, chemokines and additional immunostimulatory molecules. In limited infections, the response to lipid A helps to clear the bacteria, but in overwhelming sepsis, high levels of circulating cytokines and procoagulant activity may damage the microvasculature and precipitate the syndrome of Gram-negative septic shock with disseminated intravascular coagulation.

No conclusive evidence for a protective role of LPS in pertussis vaccines is available, although passive immunization experiments in mice have demonstrated that antibodies against LPS can confer a level of protection. In addition and more importantly, the presence of LPS in a vaccine however does provide adjuvant activity by enhancing the immune response against other antigens (K. Mills: Immunity to *Bordetella pertussis*. Microbes and Infection 3: 655-677 (2001).

Concerns about safety have adversely affected vaccine uptake and have motivated the development of acellular pertussis vaccines, prepared with highly purified antigens from *B. pertussis*. In recent years, besides the so-called "whole cell vaccines" or "WCV's", also acellular vaccines or "ACVs" have now been introduced in several countries.

Acellular vaccines normally comprise of 1 to 3 or more antigens of the pathogenic organism. In the case of *B. pertussis* antigens commonly used are: pertussis toxin (PT, normally treated to destroy its toxicity while retaining immunogenicity), filamentous hemagglutinin (FHA), fimbriae, and the 69 kD protein or pertactin (Prn). In general the reactogenicity of acellular vaccine is much lower than the reactogenicity of whole cell vaccine. Acellular vaccine is associated with a significantly reduced frequency of systemic reactions (fever, vomiting, fretfulness, anorexia) and local reactions (swelling, redness, warmth, tenderness, stiffness, pain). However, the clinical data are still controversial whether the protective immunity of acellular vaccines matches the protective effect of whole cell vaccine. In many studies the protective effect of whole cell vaccines is superior and a debate is ongoing whether this outweighs the risk of rare but serious adverse effects of whole cell vaccines in infants. Currently various immunizations schemes are being tested, wherein up to six doses of acellular vaccine are given. The whole cell vaccine was initially given 5 times, incorporated with the routine vaccines schedule with the last booster given between 4-6 years of age. The acellular pertussis vaccine is now recommended to be given 6 times including a last dose (combined with the diphtheria-tetanus vaccine) during the teenage years. The acellular vaccine appears to be safer than the whole cell-based vaccine, but both should not be given to children with a previous allergic reaction to the pertussis vaccine The adverse side effects of pertussis whole cell vaccines have been well documented in the art (review: S. H. Yeh: Pertussis: persistent pathogen, imperfect vaccines. Expert Rev. Vaccines 2: 113-127 (2003). Although currently used acellular vaccines in part overcome these adverse side effects, the protective immunity provided by these vaccines is still controversial and leaves much room for improvement. Importantly, in a mouse model superior long-term protection was found with whole-cell as compared to acellular vaccines (K. Mills: Immunity to *Bordetella pertussis*. Microbes and Infection 3: 655-677 (2001)). Moreover, acellular vaccines are more costly and difficult to produce, requiring isolation, extensive purification and quality control of various antigens and mixing and formulating them in optimal/desired quantities. There is clearly a long felt need for better *B. pertussis, B. parapertussis, B. bronchiseptica* and other Gram negative vaccines.

DETAILED DESCRIPTION OF THE INVENTION

The current invention provides methods and means for the preparation of improved pertussis vaccines. The invention discloses novel *Bordetella* proteins. These novel *B. pertussis, B. parapertussis* and *B. bronchiseptica* proteins and DNA molecules encoding these proteins are used according to the invention to modify lipid A and thereby provide new *B. pertussis, B. parapertussis* and *B. bronchiseptica* bacterial strains and other Gram negative bacterial cells, comprising at least partially 3-O-deacylated and detoxified LPS. The current invention also provides improved compositions for vaccination, comprising *Bordetella* species bacterial cells comprising partially 3-O-deacylated LPS, pharmaceutical compositions comprising isolated and at least partially 3-O-deacylated LPS or in vitro 3-O-deacylated LPS. The invention further provides antibodies raised against and specific for 3-O-deacylated lipid A and/or LPS molecules.

Lipopolysaccharide (LPS), a major component of the Gram-negative bacterial outer membrane, is known to be important for the functioning of this membrane as a permeability barrier and for the resistance against complement-mediated cell lysis (reviewed in 1). It consists of three covalently linked domains: lipid A, the core, and the O-antigen. Lipid A forms the hydrophobic membrane anchor and is responsible for the endotoxic activity of LPS. In *Escherichia coli*, it consists of a 1,4'-bisphosphorylated β-1,6-linked glucosamine disaccharide, which is substituted with R-3-hydroxymyristic acid residues at positions 2, 3, 2', and 3' via ester or amide linkage. Secondary lauroyl and myristoyl groups substitute the hydroxyl group of R-3-hydroxymyristoyl at the 2'- and 3'-positions, respectively (FIG. 1A). Previous studies have shown that the phosphate groups, the glucosamine disaccharide, and the correct number and length of the acyl chains are important for the biological activity of lipid A (1, 2, 3).

Figure 1B:
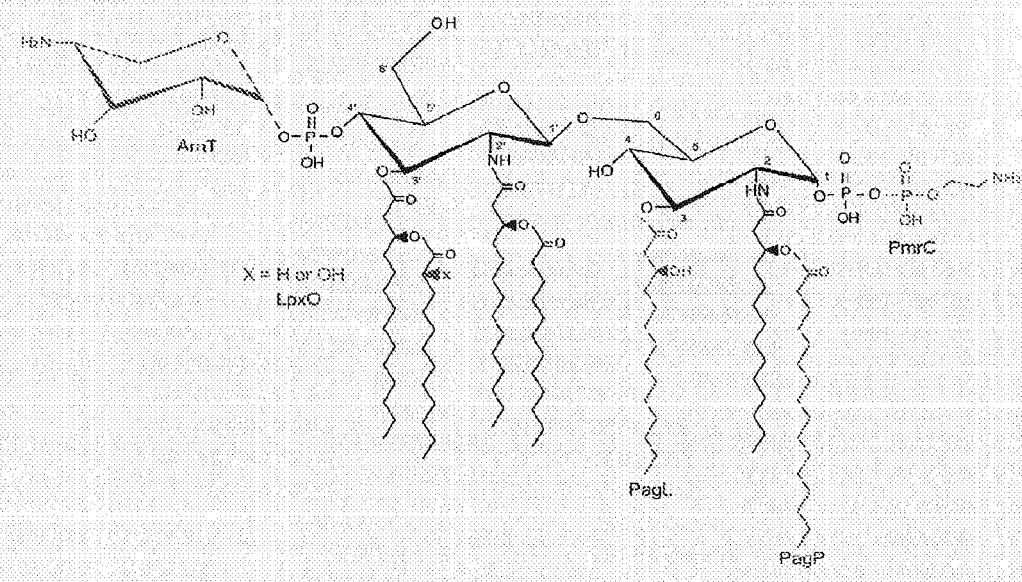

The basic structure of lipid A is reasonably well conserved among Gram-negative bacteria, although slight variations in the pattern of the substitutions of the two phosphates and the acyl-chain number and length are observed (4, 5). Additional modifications of lipid A (FIG. 1B) are regulated in *Salmonella enterica* serovar *Typhimurium* (*S. Typhimurium*) by the two-component regulatory system PhoP/PhoQ (6, 7). In response to low $Mg^{2+}$ levels, the sensor kinase PhoQ phosphorylates and thereby activates the transcriptional activator PhoP, which leads to the activation or repression of 40 different genes (6, 8). A second regulatory system involved in lipid A modification is the PmrA/PmrB two-component system, which itself is PhoP/PhoQ regulated (9, 10). Mutants with alterations in the PhoP/PhoQ system exhibit reduced virulence and an increased susceptibility to anti-microbial peptides (11, 12). Homologs of the PhoP/PhoQ and PmrA/PmrB systems have been identified in other Gram-negative bacteria, including *E. coli, Yersinia pestis*, and *Pseudomonas aeruginosa* (13, 14).

Up till now, several lipid A-modifying enzymes have been identified. Substitution of the 1 and 4' phosphate groups with one or two 4-amino-4-deoxy-L-arabinose (L-Ara4N) moieties in *S. Typhimurium* was found to be dependent on the enzyme ArnT (15). Recently, the PmrC protein was identified to mediate the addition of phosphoethanolamine (pEtN) to lipid A in *Salmonella enterica* (16). Another enzyme, designated LpxO, catalyzes the $O_2$-dependent hydroxylation of lipid A (17), and a lipid A 1-phosphatase was identified in *Rhizobium leguminosarum* (18). All these enzymes are thought to reside within the inner membrane or periplasmic space (15, 16, 17, 18). Recently, a new class of outer membrane-localized lipid A-modifying enzymes was discovered. One of them is the palmitoyl transferase PagP (19). Palmitoylation of lipid A leads to an increased resistance to cationic anti-microbial peptides (7). Furthermore, palmitoylated lipid A antagonizes LPS-induced activation of human cells (20). Homologs of PagP are found, amongst others, in *S. Typhimurium, Bordetella pertussis, Bordetella bronchiseptica, Bordetella parapertussis, Legionella pneumophila, E. coli*, and *Y. pestis* (19, 21).

Another outer membrane-localized lipid A-modifying enzyme is the 3-O-deacylase PagL (22). This enzyme was discovered in *S. Typhimurium* and shown to hydrolyze the ester bond at the 3 position of lipid A, thereby releasing the primary 3-hydroxymyristoyl moiety (22). Thus far, no obvious homologs of pagL could be found in the nonredundant or unfinished microbial databases, except in the closely related species *Salmonella typhi* and *Salmonella paratyphi* (22). Nevertheless, some other Gram-negative bacteria, including *P. aeruginosa* (14), *R. leguminosarum* (23), *Helicobacter pylon* (24), and *Porhyromonas gingivalis* (25) contain 3-O-deacylated lipid A species, suggesting that these organisms contain enzymes with a similar activity as PagL.

The current invention discloses the identification of pagL homologs in a variety of Gram-negative bacteria. Limited sequence similarity between the various proteins and advanced bioinformatics tools were used to identify these homologs and their active-site residues. In this specification, we describe the presence and use of pagL homologs for heterologous expression in a variety of Gram-negative bacteria. Although the overall sequence similarity with known pagL genes from *Salmonella* spp. is rather low, a conserved PagL domain could be distinguished in the C-terminal region.

The prior art only describes PagL proteins from *Salmonella* spp. and discloses heterologous expression of pagL only in *E. coli* (22), resulting in deacylated LPS. No data are available in the art about the presence of pagL homologs in other Gram negatives. Heterologous pagL expression in other Gram negatives, whether PagL is functional in other Gram negatives, the effect of PagL on lipid A/LPS composition, bacterial viability, toxicity and immunogenicity in other Gram negatives are all unknown factors. Only limited data for heterologous *Salmonella* pagL expression in *E. coli* is available, where a TLR response was measured in cells which express recombinant human TLR4, which does not reflect a natural situation of Gram negative infections (Kawasaki et al., J Biol Chem. 2004).

The specification of the current invention discloses activity of the *Pseudomonas aeruginosa* and *Bordetella bronchiseptica* pagL homologs, which was confirmed upon heterologous expression in *Escherichia coli* and *Bordetella* spp., which resulted in the removal of a R-3-hydroxymyristoyl group from lipid A. The effect on biological activity of LPS was assayed with human macrophage cells. Upon deacylation by PagL, *E. coli* lipid A (but not *B. pertussis* Lipid A) underwent another modification, which was the result of the activity of the endogenous palmitoyl transferase PagP. Furthermore, a conserved histidine-serine couple as active-site residues was identified, suggesting a catalytic mechanism similar to serine hydrolases. Finally, in vitro activity of PagL on LPS substrates is demonstrated. The biological function of PagL may be applied according to the invention to modify Gram negative pathogenicity, toxicity and immunogenicity. This modification may take place on whole bacterial cells or parts, fractions or compounds derivable thereof. The invention ultimately provides novel vaccines against Gram negative bacterial infections, comprising whole cells of Gram negative bacteria according to the invention or modified lipid A/LPS obtainable and/or isolated from these bacteria, or in vitro modified LPS/lipid A molecules.

DETAILED DESCRIPTION

Definitions

"Sequence identity" is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having acidic side chains is aspartic acid and glutamic acid and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A DNA segment according to the invention is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof.

The selection of an appropriate promoter sequence generally depends upon the host cell selected for the expression of the DNA segment. Examples of suitable promoter sequences include prokaryotic, and eukaryotic promoters well known in the art (see, e.g. Sambrook and Russell, 2001, supra). The transcriptional regulatory sequences typically include a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). Expression vectors include the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, insect cells, e.g., Sf9 cells, mammalian cells, e.g., CHO cells and bacterial cells, e.g., *E. coli* or *Bordetella* spp.

In a first embodiment, the current invention provides new polypeptides comprising lipid A 3-O-deacylase activity, whereby the polypeptide exhibits at least 25, 30, 40, 50, 60, 70, 80, 90, 95, 98 or 99% amino acid identity with SEQ ID No. 1 and the polypeptide exhibits lipid A 3-O-deacylase activity as determined by the assays described in this specification, in vivo as exemplified in example 3 or in vitro according to example 9. Preferably the polypeptide having lipid A 3-O-deacylase activity is the polypeptide according to SEQ ID No. 1, the PagL protein of *Bordetella bronchiseptica* and *Bordetella parapertussis*, or a part thereof, a mutant thereof, or a fusion protein comprising at least a part of SEQ ID No. 1 comprising the lipid A 3-O-deacylase activity.

In another embodiment the current invention comprises a nucleic acid sequence encoding the polypeptide exhibiting at least 25, 30, 40, 50, 60, 70, 80, 90, 95, 98 or 99% amino acid identity with SEQ ID No. 1. Preferably, the nucleic acid sequence according to the invention exhibits at least 50, 60, 70, 80, 90, 95, 98 or 99% identity with the nucleic acid sequence according to SEQ ID No's 2 or SEQ ID No. 3, the pagL genes from *B. bronchiseptica* and *B. parapertussis*, respectively. The nucleic acid sequence may be a full length coding sequence or may be coding or non-coding (or complementary) parts, fragments or even oligonucleotides derived thereof.

The invention further comprises DNA vectors comprising the nucleic acid sequences according to the invention and/or encoding polypeptides exhibiting at least 25, 30, 40, 50, 60, 70, 80, 90, 95, 98 or 99% amino acid identity with SEQ ID No. 1. DNA vectors according to the invention may be any vector known in the art, such as, but not limited to: plasmids, phages, phagemids, cosmids, artificial chromosomes, vectors for (homologous) genomic integration. The vectors may contain markers, such as selectable markers, providing antibiotic resistance, fluorescent labels, molecular tags etc. Methods for cloning nucleic acids and expression of encoded proteins according the invention are known to the skilled artisan and may for instanced be found in Sambrook et al., Molecular Cloning, Cold Spring Harbor Laboratory Press, NY 1989 and Ausubel F. et al., ed., Current Protocols in Molecular Biology, Wiley Interscience, 2004. Preferably the vector according to the current invention is a vector wherein the nucleic acid sequence is operably linked to regulatory sequences such as promoters, enhancers and terminators, providing expression of the gene and translation of the messenger into the lipid A 3-O-deacylase protein. Most preferably the vector is capable of conferring expression and lipid A 3-O-deacylase activity to a Gram negative bacterial host cell, optionally in an inducible fashion, for instance by the inducible tac promoter on plasmid pMMB67.

The invention also provides antibodies capable of binding to the polypeptide according to SEQ ID No.1. Antibodies according to the invention may be monoclonal antibodies or polyclonal antibodies, raised in a host by injecting polypeptides according to the invention, as shown in the examples. Antibodies may be used for diagnostic purposes, for instance for analyzing expression of PagL proteins and mutants or homologs thereof in Gram negative bacteria. Antibodies may also be used for isolation and/or purification of proteins exhibiting lipid A 3-O-deacylase activity.

In another aspect the invention pertains to Gram negative bacteria comprising a nucleic acid molecule according to the invention and/or encoding a polypeptide molecule according to the invention. Preferably the nucleic acid molecule is comprised within a DNA vector according to the invention, providing expression of the encoded protein in Gram negative bacterial cells and providing a source of lipid A 3-O-deacylase activity to the cell. Preferably said Gram negative bacterium is a bacterium which does not comprise in its genome a gene encoding a functional protein exhibiting lipid A 3-O-deacylase activity such as a protein having significant (>40 percent) identity with a PagL protein as in SEQ ID No. 1. Most preferably, providing a source of lipid A 3-O-deacylase activity will alter the composition of the LPS in the outer membrane of the cell wall of the Gram negative bacterial cell. The Gram negative bacterium to be provided with a source of lipid A 3-O-deacylase activity may also be a bacterium comprising a non functional gene, having significant homology with a nucleic acid sequence as provided in SEQ ID No's 2 or 3, for instance by a mutation, frame shift or deletion, such as *Bordetella pertussis*.

However, also a Gram negative bacterium that does comprises a (partly) functional gene in its genome encoding a protein having lipid A 3-O-deacylase activity, may be provided with an additional source for this activity within the scope of this invention. Gram negative bacteria may have a certain level of lipid A 3-O-deacylase activity but said activity may be enhanced by providing additional and/or enhanced expression of a polypeptide according to the invention. Preferably this will result in a temporary or permanent increase in lipid A 3-O-deacylase activity in the bacterium to such an extent that the lipid A and/or LPS composition of the bacterium is temporary or permanently altered or modified, as compared to the wildtype bacterium. Such a Gram negative bacterium may for instance be a *Bordetella parapertussis* or a *Bordetella bronchiseptica* bacterium, but any other Gram negative bacterium, preferably a pathogenic Gram negative bacterium, may be chosen, for example *Neisseria* spp., such as *N. meningitidis, N. gonorrhoeae, N. lactamica.*

A Gram negative bacterium according to the invention comprising lipid A 3-O-deacylase activity or elevated levels of lipid A 3-O-deacylase activity preferably comprises at least partially 3-O-deacylated lipid A and/or LPS species in the outer membrane of the bacterial cell wall. Alternatively the Gram negative bacterium according to the invention may comprise LPS or lipid A species carrying a secondary modification after the 3-O-deacylation of lipid A, such as palmitoylation, dephosphorylation or any other secondary modification after 3-O-deacylation of lipid A. The bacterial cell according to the invention may comprise at least 10, 20, 30, 40, 50, 60, 70, 80 or 90 percent of its total LPS/lipid A in 3-O-deacylated form, or may alternatively comprise at least 10, 20, 30, 40, 50, 60, 70, 80 or 90 percent of its lipid A/LPS in a form carrying a secondary modification, such as for example, but not limited to, palmitoylation or dephosphorylation.

In another aspect the current invention provides methods for producing partially 3-O-deacylated LPS. In a first embodiment, such a method comprises the step of culturing the Gram negative bacterium according to the invention under conditions conducive to synthesis of the deacylated LPS, and optionally, recovery of the deacylated LPS. Methods for culturing various Gram negative bacteria are known in the art and may for instance be found in Methods for General and Molecular Bacteriology. P. Gerhardt et al., Eds. American Society for Microbiology, Washington D.C., 1994. Methods for recovery, isolation and/or purification of LPS are also known in the art (Meningococcal Vaccines, Methods and Protocols. A. J. Pollard and M. C. J. Maiden, Eds. Chapter 12: Construction of LPS mutants, pp. 155-165. Humana Press, Totowa, N.J., 2001) and may for instance be carried out according to the examples provided in this specification.

Alternatively the current invention provides a method for producing at least partially 3-O-deacylated LPS or lipid A in vitro, the method comprising the steps of providing a composition comprising LPS or lipid A in crude or (partially) purified form and bringing this composition into contact with a polypeptide or protein according to the invention under conditions conducive to enzymatic 3-O-deacylation in vitro. Such conditions can be found in the current specification, in example 9 and in the methods section.

In yet another embodiment the current invention provides compositions comprising at least partially 3-O-deacylated LPS and/or lipid A, preferably comprising at least 10, 20, 30, 40, 50, 60, 70, 80, 90, 95, 98 or 99 percent of the total LPS or lipid A in its 3-O-deacylated form or in another form carrying a secondary modification after 3-O-deacylation, such as a palmitoylated form.

Compositions according to the invention, comprising partially 3-O-deacylated LPS and/or lipid A and optionally carrying secondary modifications, either comprised in the outer membrane of the cell wall of bacterial cells, or in crude or purified forms, may be used for the manufacture of pharmaceutical compositions. In a particularly preferred embodiment, such pharmaceutical compositions according to the invention may be compositions suitable for vaccination purposes. Such pharmaceutical compositions are capable of eliciting an immune response in a host organism, preferably a mammal, more preferably a human, against a Gram negative bacterium. The presence of at least partially 3-O-deacylated LPS and/or lipid A or alternatively LPS carrying secondary modifications after 3-O-deacylation, provides several advantages, such as the advantage of a reduced toxicity, a reduced number and reduced severity of side effects in the subject and a higher tolerated dose for the composition in the subject to be treated or vaccinated. The pharmaceutical composition may contain 1 or more excipients and/or adjuvants. Pharmaceutically acceptable excipients and adjuvants are known in the art and may be freely chosen by the skilled person, for instance from: Current protocols in Immunology, Wiley Interscience 2003 or Remington's Pharmaceutical Sciences, 18$^{th}$ ed., Mack Publishing Company, 1990.

In a first embodiment the pharmaceutical composition may be a whole cell vaccine, comprising live or live attenuated bacterial cells or non-viable bacterial cells, which may have been inactivated by freezing, heat treatment, mechanical disruption, chemical treatment or other methods known in the art of pharmacy and vaccination (J. L. Pace, H. A. Rossi, V. M. Esposito, S. M. Frey, K. D. Tucker, R. I. Walker. Inactivated whole-cell bacterial vaccines: current status and novel strategies. Vaccine 16: 1563-1574 (1998)). Preferably the bacterial cell is a Gram negative, pathogenic bacterial cell, more preferably the bacterial cell is of the genera *Bordetella, Salmonella, Shigella, Neisseria, Klebsiella, Pseudomonas, Haemophilus, Escherichia, Proteus* and most preferably is *Bordetella pertussis, Bordetella parapertussis* or *Bordetella bronchiseptica*.

In an second preferred embodiment, the pharmaceutical composition according to the invention may be an a-cellular vaccine, comprising of 1, 2, 3 or more immunogenic components of the Gram negative pathogenic bacterium and comprising at least partially 3-O-deacylated LPS or lipid A, or said LPS carrying secondary modifications after 3-O-deacylation. Preferably the partially 3-O-deacylated lipid A and/or LPS is obtained from a Gram negative, pathogenic bacterial cell according to the invention, wherein preferably the bacterial cell is of the genus *Bordetella*, and most preferably is *Bordetella pertussis, Bordetella parapertussis* or *Bordetella bronchiseptica*. The at least partially 3-O-deacylated lipid A and/or LPS, optionally carrying secondary modification after deacylation, may be used for eliciting a protective immune response against the bacterium producing it, but alternatively may also be used and admixed to other compositions for use as a suitable adjuvant substance. LPS is known in the art to be a suitable adjuvant for vaccination purposes, activating Toll like receptors and stimulating an innate immune response. Partially 3-O-deacylated and at least partially detoxified LPS and/or lipid A according to the invention largely retains this immune stimulating (adjuvant) activity, while causing less toxicity related adverse side effects, such as local swelling, redness, pain and fever.

Pharmaceutically acceptable composition and vaccines according to the invention may be used in methods of treatment of subjects suffering from or at risk of acquiring a pathogenic, Gram negative bacterial infection, comprising administering the pharmaceutical composition, a whole cell or an a-cellular vaccine according to the invention. The use of specific adjuvants, the relative and absolute amounts of substances in the compositions and the doses regimen for the administration are known or may be determined by the skilled person and may be adapted for the circumstances such as the particular pathogenic infection or the status of the particular subject to be treated. The doses regimen may comprise a single dose but may also comprise multiple doses, for instance booster doses and may be administered orally, intranasally or parenterally. Various doses regimens for vaccination purposes are known in the art and and may be suitably adapted by the skilled person.

FIGURE LEGENDS

FIG. 1. Lipid A architecture. A, *E. coli* lipid A consists of a bisphosphorylated glucosamine disaccharide substituted with four R-3-hydroxymyristoyl moieties, of which the 2' and 3' fatty-acyl chains are esterified with laurate and myristate, respectively. B, Regulated modifications of *Salmonella* lipid A. Substitution of the phosphate moieties with L-Ara4N or pEtN is mediated by ArnT and PmrC, respectively, the formation of a 2-hydroxymyristate-modified lipid A by LpxO, the addition of a secondary palmitoyl chain at the 2-position by PagP, and the removal of the 3-hydroxymyristoyl moiety at the 3-position by PagL.

FIG. 2. Multiple sequence alignment of the PagL proteins. Sequences were aligned using ClustalW (World wide web URL of ch.embnet.org/software/ClustalW.html). Hyphens indicate gaps introduced for optimal alignment. Absolutely conserved residues are marked with asterisks. Indicated by colons and dots are strongly and weakly conserved residues, respectively. The pagL ORF in *B. pertussis* is disrupted by a frame shift, which was restored for this alignment by adding two nucleotides in codon 33 (SEQ ID NO:1). The GenBank protein accession numbers for the PagL homologs are: *S. Typhimurium* AAL21147 (SEQ ID NO:17), *B. bronchiseptica* NP_890306 (SEQ ID NO:1), *B. parapertussis* NP_885487, (SEQ ID NO:1) *B. pertussis* BX470248$^§$ (SEQ ID NO:1), *P. aeruginosa* NP_253350 (SEQ ID NO:6), *P. fluorescens* NZ_AAAT03000006$^§$ (SEQ ID NO:7), *P. putida* NC_002947$^§$ (SEQ ID NO:9, SEQ ID NO:10) S, *P. syringae* ZP_00125465 (SEQ ID NO8, *B. fungorum* NZ_AAAJ03000003$^§$ (SEQ ID NO:11), *B. mallei* NC_002970$^§$ (SEQ ID NO:12), *B. pseudomallei* NC_002930$^§$ (SEQ ID NO:13), *R. metallidurans* ZP_00274744 (SEQ ID NO:15), *R. solanacearum* NP_522762 (SEQ ID NO:16), and *A. vinelandii* ZP_00089534 (SEQ ID NO:14). The symbol § indicates GenBank Accession Numbers of whole (unfinished) genomes, in which the PagL homologs were manually identified.

Figure 3:
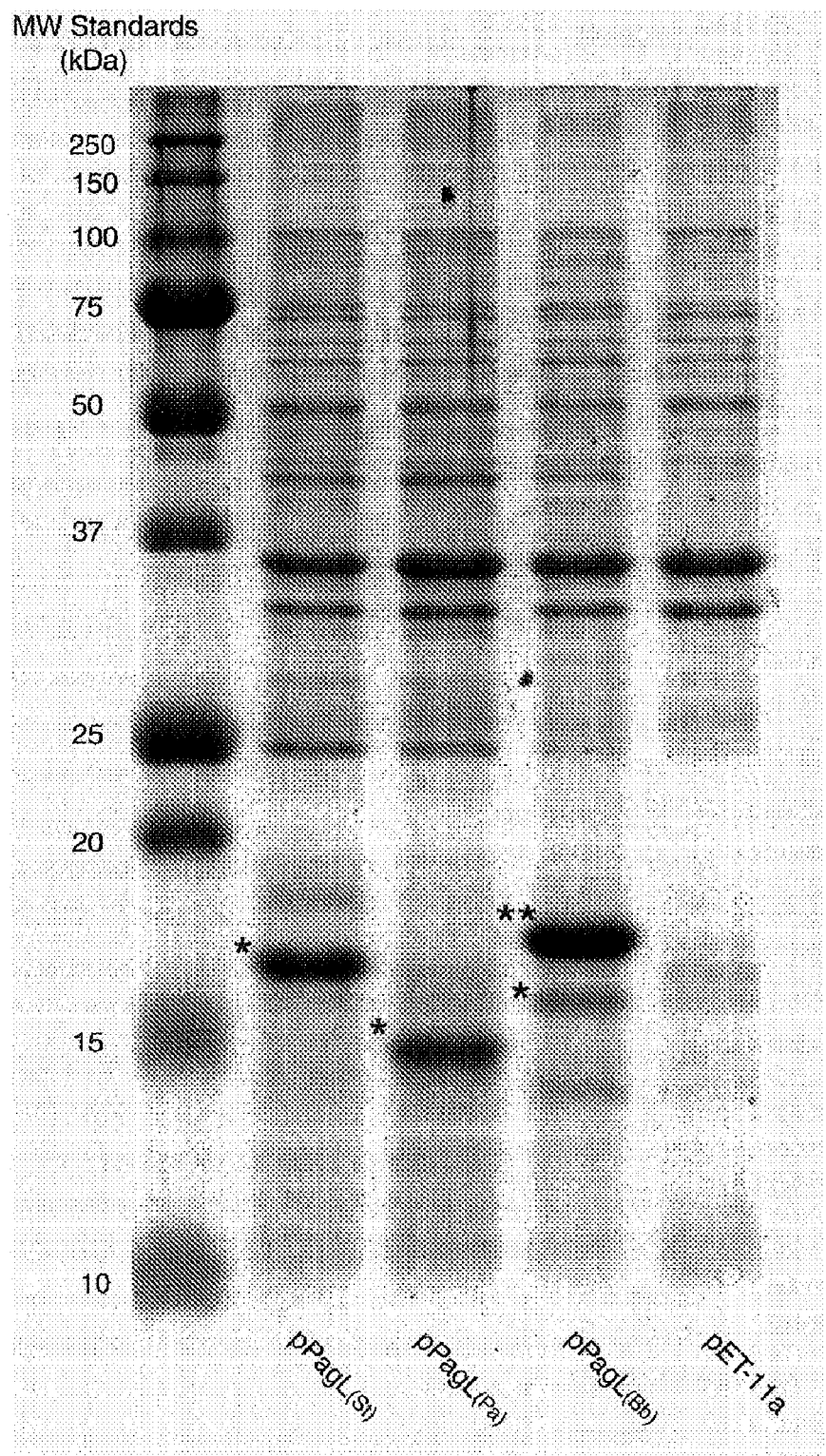

FIG. 3. Expression and membrane localization of PagL in *E. coli* BL21 Star™ (DE3). Membranes from *E. coli* BL21 Star™ (DE3) containing empty pET-11a or the pPagL plasmids were isolated and analyzed by SDS-PAGE. Proteins were stained with Coomassie Brilliant Blue. Asterisks indicate the bands that were subjected to microsequencing and were found to correspond to the mature PagL proteins. The band indicated by the double asterisk corresponds to the PagL$_{(Bb)}$ precursor protein. Molecular weight standard proteins are present on the left side.

Figure 4:
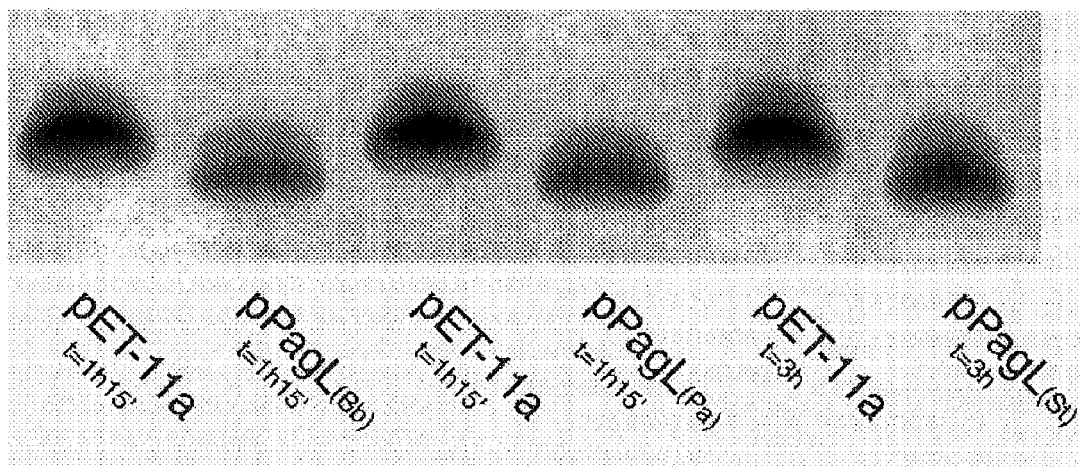

FIG. 4. Analysis by Tricine-SDS-PAGE of LPS modification in vivo. Exponentially growing *E. coli* BL21 Star™ (DE3) cells containing pET-11a or the pPagL constructs were induced with IPTG for the indicated time, after which 1 OD$_{600}$ unit culture samples were collected and analyzed by Tricine-SDS-PAGE.

Figure 5:
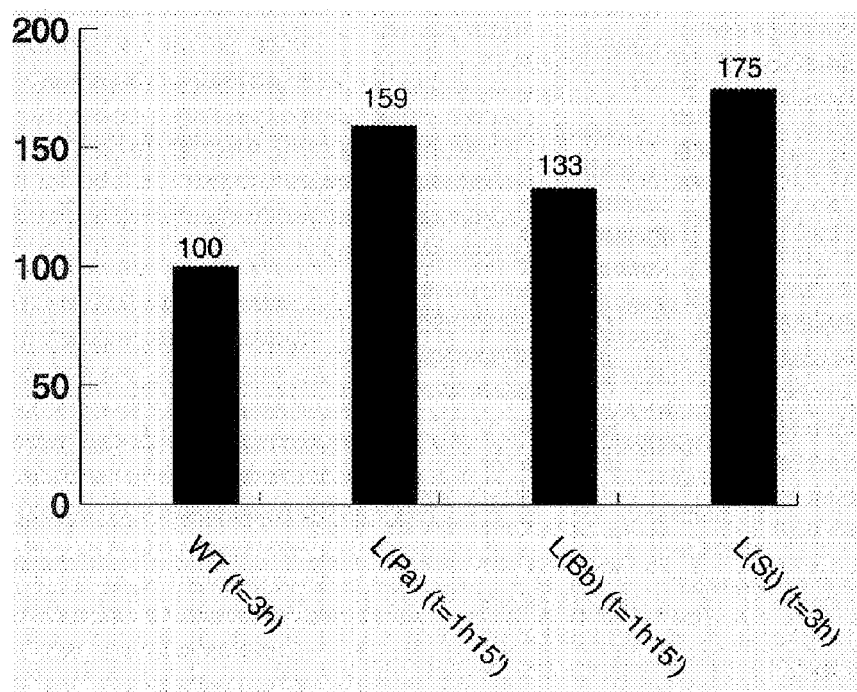

FIG. 5. GC/MS analysis of wild-type and PagL-modified *E. coli* BL21 Star™ (DE3) LPS. GC/MS analysis of purified *E. coli* BL21 Star™ (DE3) wild-type LPS (WT), PagL$_{(St)}$-modified LPS (L(St)), PagL$_{(Bb)}$-modified LPS (L$_{(Bb)}$), and PagL$_{(Pa)}$-modified LPS (L$_{(Pa)}$) (t=time after induction). Indicated are the normalized C14/C14-3OH ratios with wild-type LPS set at 100 (values shown above bars).

FIG. 6. Structural analysis by ESI-MS of wild-type and PagL-modified *E. coli* BL21 Star™ (DE3) LPS. Lipid A species from wild-type *E. coli* BL21 Star™ (DE3) containing empty pET-11a (A), and lipid A species modified by PagL$_{(St)}$ (B), PagL$_{(Pa)}$ (C), and PagL$_{(Bb)}$ (D) were analyzed by ESI-MS. Major peaks at m/z 1797, 1928, 1622, and 1490 were interpreted as the characteristic hexa-acylated bis-phosphate species that is typically found in *E. coli*, a hexa-acylated bis-phosphate species substituted with an L-Ara4N moiety, a 3-O-deacylated mono-phosphate species substituted with an L-Ara4N moiety, and a 3-O-deacylated mono-phosphate species, respectively. The major peaks at m/z 1716 and 1847 probably represent fragment ions of the species at m/z 1797 and 1928.

Figure 7:
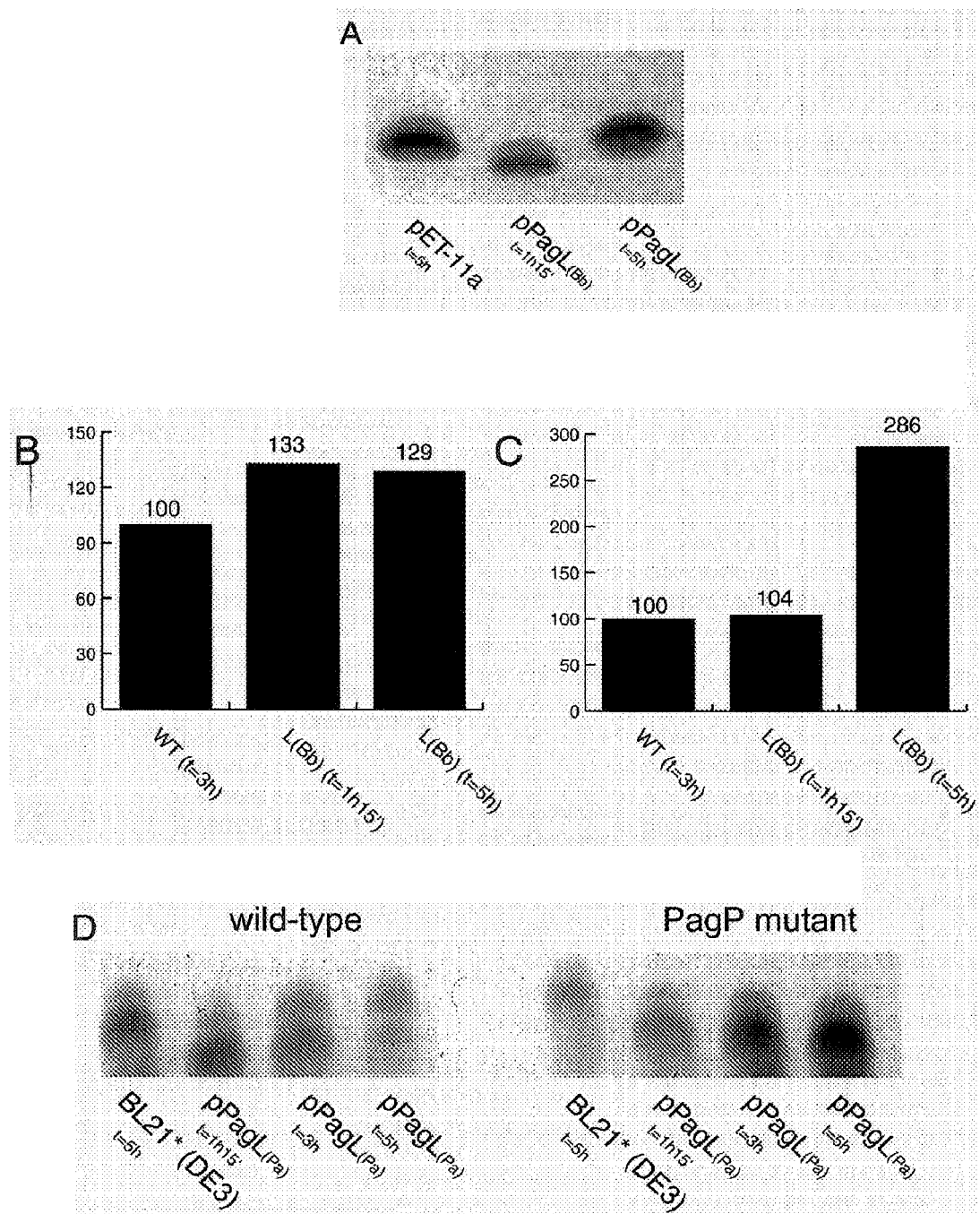

FIG. 7. In vivo re-modification of deacylated LPS and the role of endogenous PagP. A, Exponentially growing *E. coli* BL21 Star™ (DE3) cells containing the empty pET-11a vector or the pPagL$_{(Bb)}$ plasmid were induced with IPTG for the indicated time period. Samples corresponding to 1 OD$_{600}$ unit were collected and analyzed by Tricine-SDS-PAGE. B and C, The fatty acid content of purified *E. coli* BL21 Star™ (DE3) wild-type LPS (WT) and PagL$_{(Bb)}$-modified LPS (L(Bb)), isolated at the indicated time after induction of pagL expression, was analyzed by GC/MS. Indicated are the normalised C14/C14-3OH (B) and C16/C14 (C) ratios with wild-type LPS set at 100 (values shown above bars). D, Exponentially growing wild-type *E. coli* BL21 Star™ (DE3) or *E. coli* BL21 Star™ (DE3) and its pagP mutant derivative JG101, containing pPagL$_{(Pa)}$, were induced with IPTG for the indicated time period, after which 1 OD$_{600}$ unit culture samples were collected and analyzed on Tricine-SDS-PAGE gel.

Figure 8:
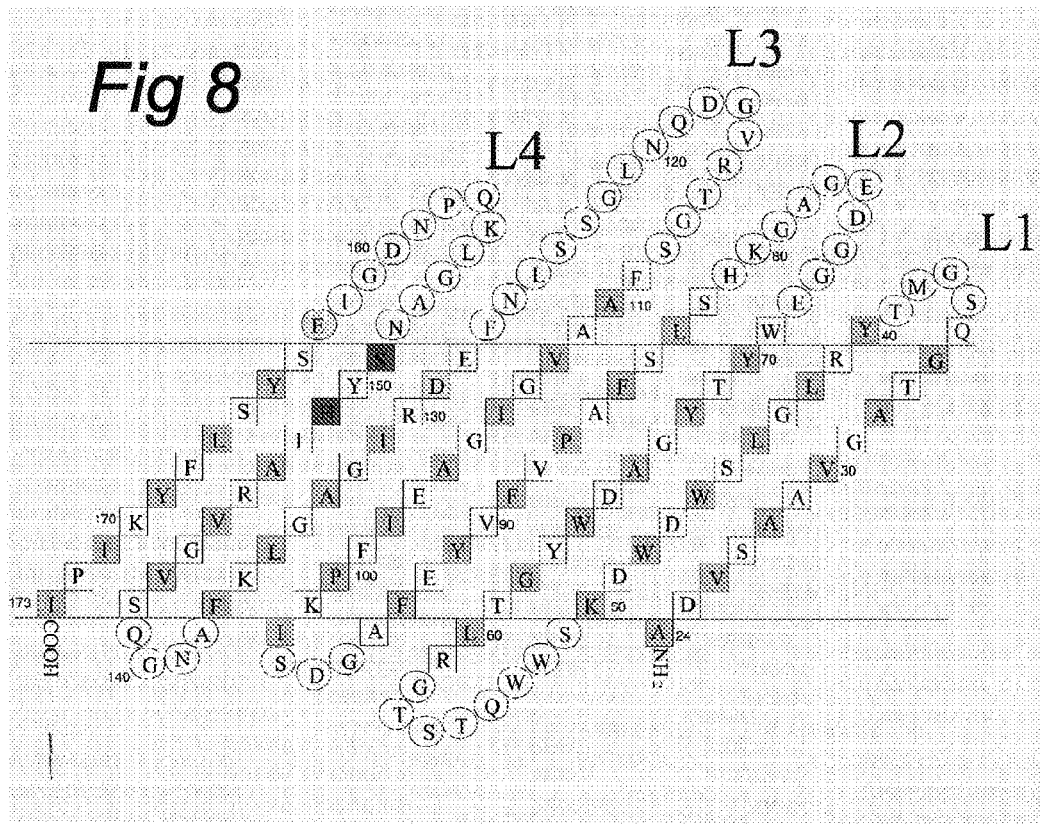

FIG. 8. Topology model for PagL from *P. aeruginosa*. A model for the topology of PagL$_{(Pa)}$ was constructed using the general rules of outer membrane protein architecture as described in (44). The proposed model consists of an eight-stranded β-barrel with four loops (L1-4) extending into the external environment. Residues in the postulated β-strands are shown in diamonds, which are shaded for residues that are exposed to the lipid bilayers. His$_{149}$ and Ser$_{151}$ (marked in red; position in the PagL$_{(Pa)}$ precursor) are absolutely conserved (FIG. 2) and are suggested to be part of a 'classical' catalytic triad of a serine hydrolase. Potential candidates for the acidic residue of the catalytic triad are indicated in yellow. Numbers refer to the position of the residues in the precursor sequence.

FIG. 9. Identification of PagL$_{(Pa)}$ active-site residues by amino acid substitution. Exponentially growing *E. coli* BL21 Star™ (DE3) cells containing the empty pET-11a vector, the pPagL$_{(Pa)}$ plasmid, or the mutant pPagL$_{(Pa)}$ plasmids were induced with IPTG for 75 min, after which 1 OD$_{600}$ unit culture samples were collected and analyzed by SDS-PAGE followed by immunoblotting with primary antibodies against PagL$_{(Pa)}$ (A) and by Tricine-SDS-PAGE to visualize LPS (B).

Figure 10A:
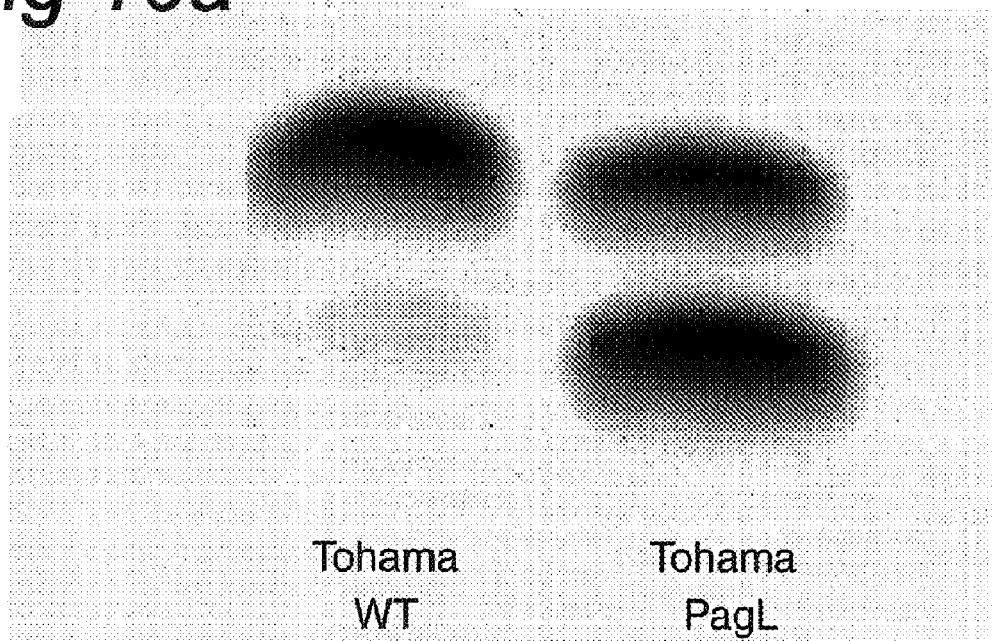
Figure 10B:
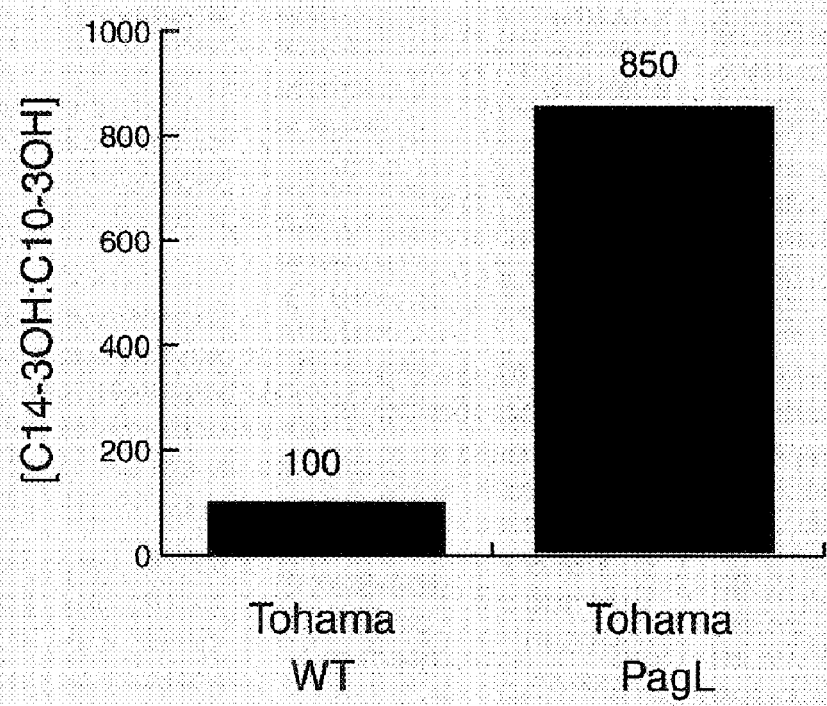

FIG. 10. In vivo modification of *B. pertussis* LPS. A, LPS from wild-type *B. pertussis* strain Tohama or *B. pertussis* strain Tohama carrying the pMMB67EH-PagL$_{(Bb)}$ plasmid was isolated and analyzed by Tricine-SDS-PAGE. B, The fatty acid content of purified *B. pertussis* strain Tohama wild-type LPS (WT), and PagL$_{(Bb)}$-modified LPS (PagL) was analyzed by GC/MS. Indicated is the normalised C14-3OH/C10-3OH ratio with wild-type LPS set at 100 (values shown above bars).

Figure 11A:
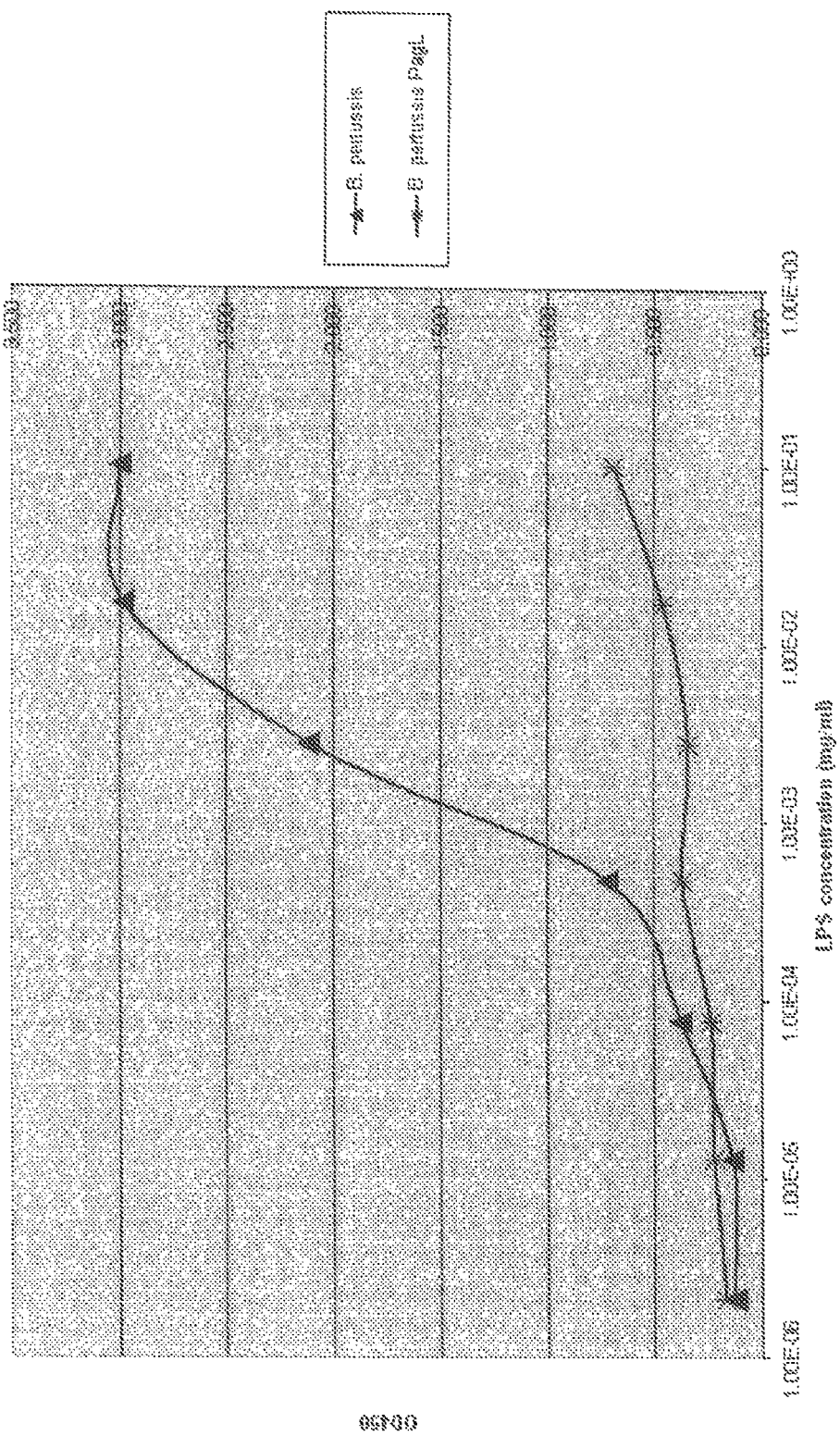
Figure 11B:
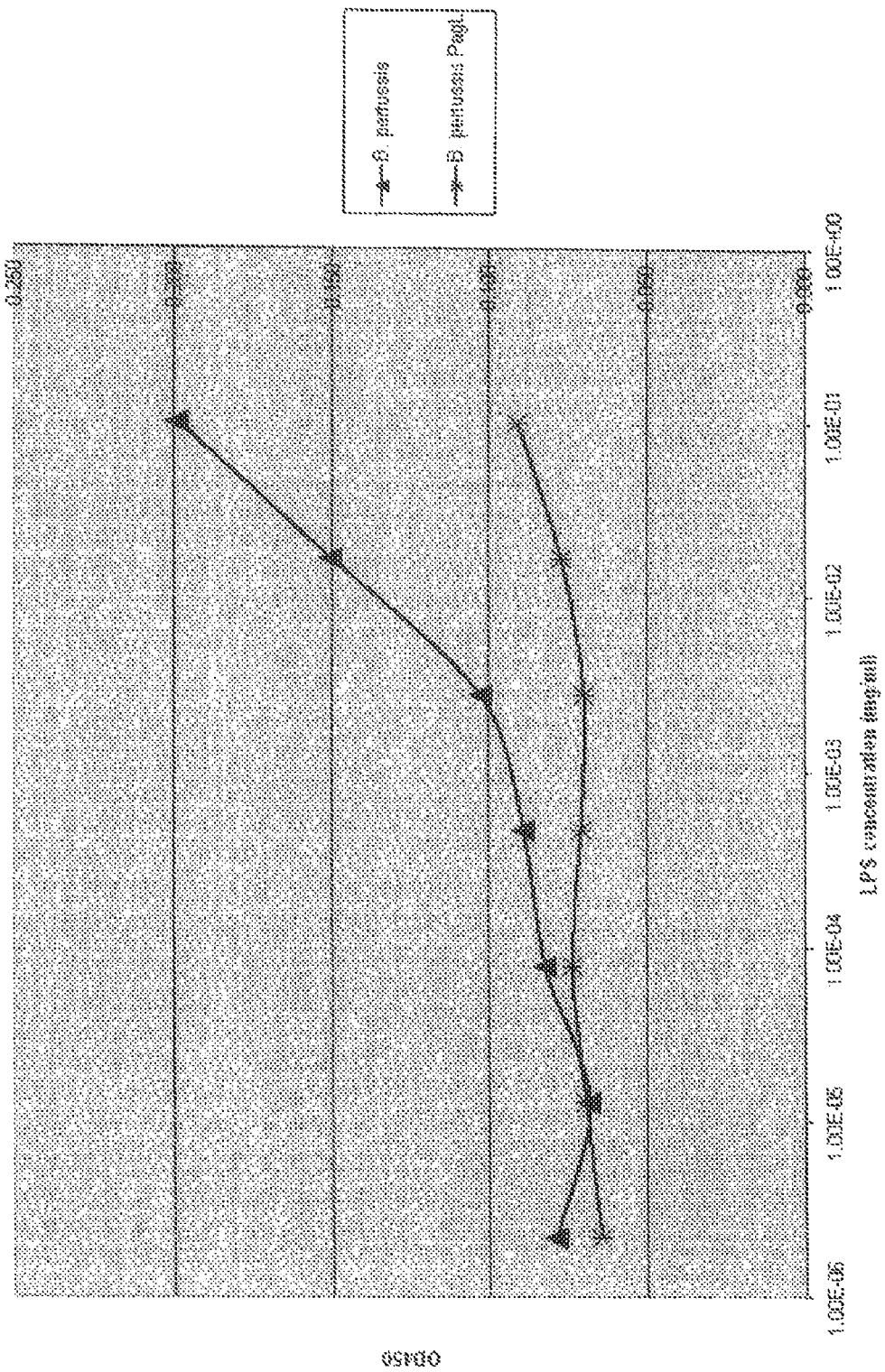

FIG. 11. Biological activity of isolated LPS. IL-6 (A) or IL-10 (B) induction in MM6 cells by purified LPS. The horizontal axes give the LPS concentration in mg/ml and the vertical axes give the ELISA-read out at 450 nm.

Figure 12:
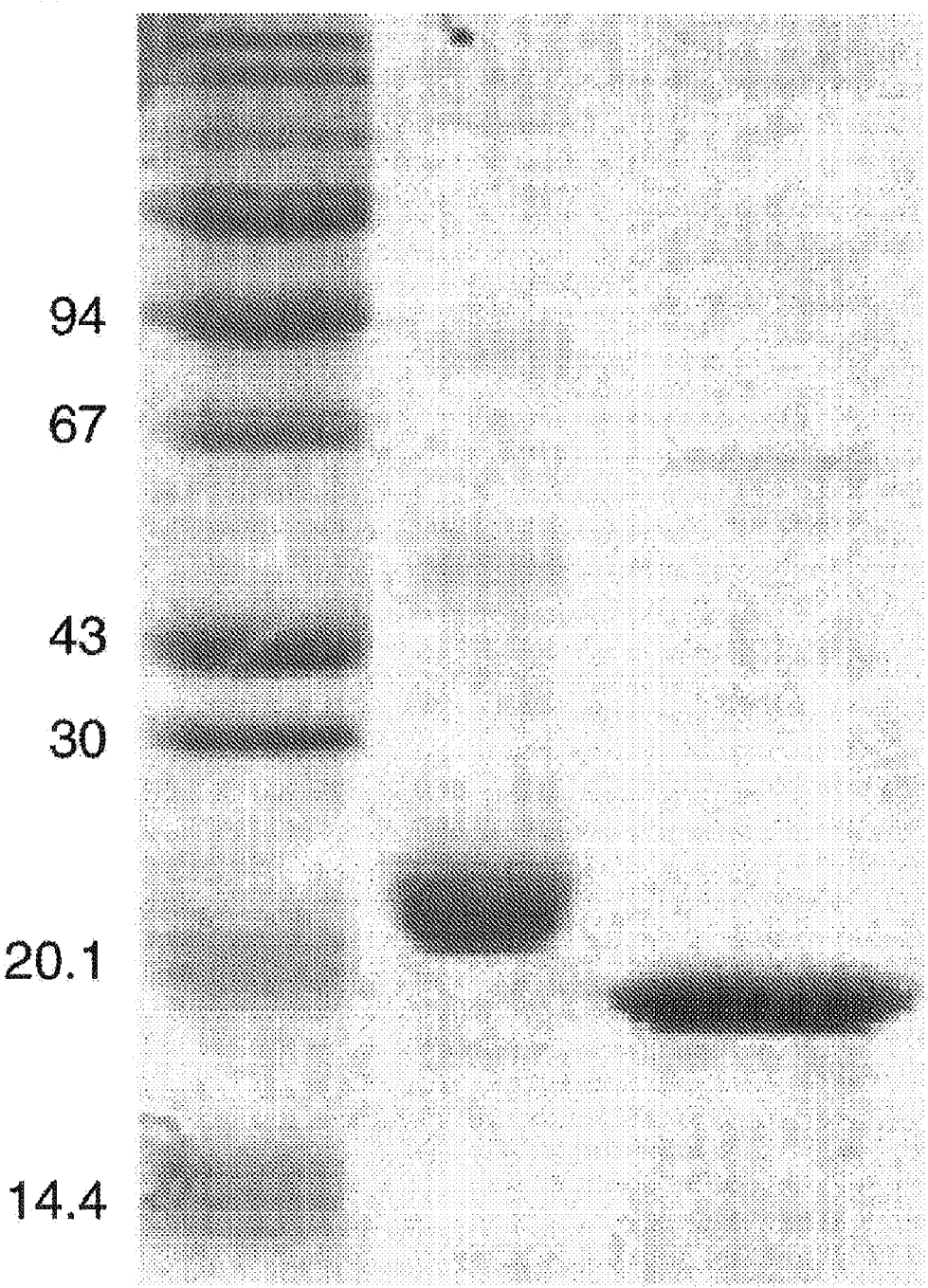

FIG. 12. Heat-modifiability of purified, refolded PagL$_{(Pa)}$ (−) analysed by semi-native SDS-PAGE. Coomassie Brilliant Blue stained semi-native SDS-PAGE gel showing the heath-modifiability of purified, refolded PagL$_{(Pa)}$(−). Samples were treated in sample buffer containing 0.1% SDS at room temperature (RT) or 2% SDS at 100° C. (15 min), prior to electrophoresis. Molecular weight standard proteins are present on the left side.

FIG. 13. In vitro LPS modification by membrane-bound or in vitro refolded PagL. Silver-stained Tricine-SDS-PAGE gels showing in vitro PagL activity. A, Purified *N. meningitidis* L3-LPS was incubated in a detergent-containing buffer for 18 h at 37° C. with or without cell envelopes prepared from *E. coli* BL21 Star™ (DE3) containing empty pET-11a, or the pPagL plasmids. B, Purified *N. meningitidis* L3-LPS was incubated in a detergent-containing buffer in the absence or presence of 5 mM EDTA for 18 h at 37° C. with or without 4 μg in vitro refolded PagL$_{(Pa)}$ without its signal sequence (PagL$_{(Pa)}$(−)). Similar amounts of assay mixes were loaded in all lanes.

Figure 14:
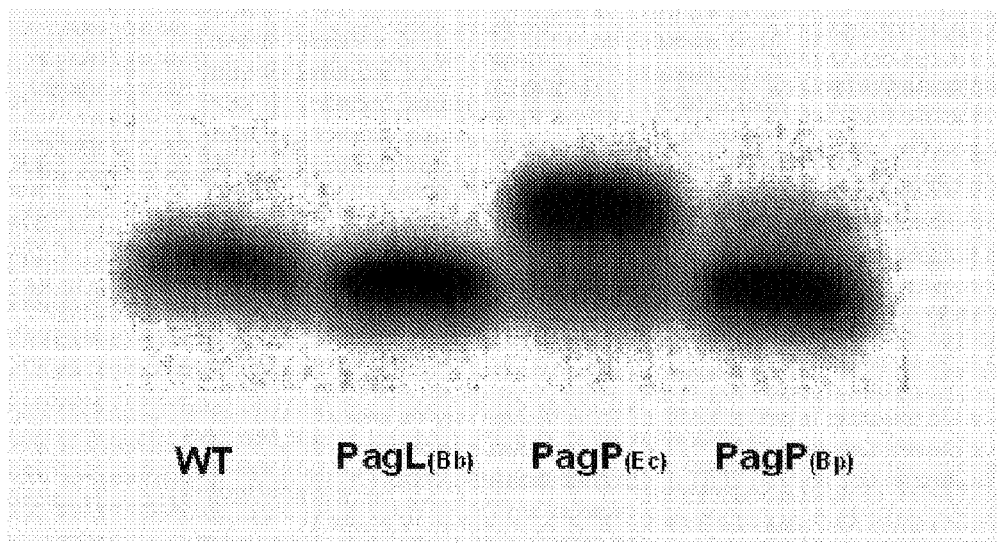

FIG. 14. Analysis by Tricine-SDS-PAGE of in vivo LPS modification. LPS was isolated from wild-type and PagP/PagL-expressing *B. pertussis* strain Tohama by hot phenol/water extraction and analysed by Tricine-SDS-PAGE.

Figure 15:
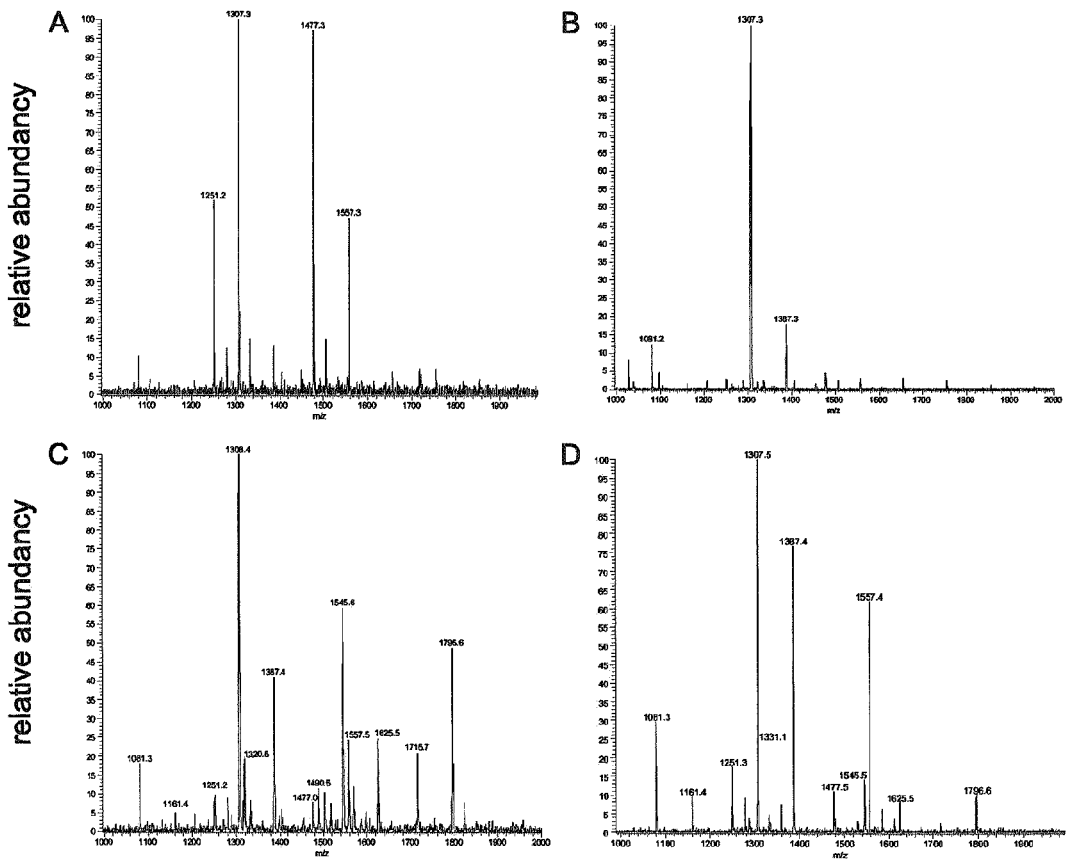

FIG. 15. Structural analysis by ESI-MS of wild-type and PagL/PagP-modified *B. pertussis* LPS. Lipid A species from wild-type *B. pertussis* strain Tohama (A), and lipid A species modified by PagL$_{(Bb)}$ (B), PagP$_{(Ec)}$ (C), and PagP$_{(Bp)}$ (D) were analysed by ESI-MS. Major peaks at m/z 1557, 1477, 1387, 1307, 1251, and 1081 were interpreted as the characteristic penta-acylated bis-phosphate species that is typically found in *B. pertussis*, the corresponding penta-acylated mono-phosphate species, the deacylated lipid A species of the molecular ion at m/z 1557 missing the primary 3-hydroxydecanoic acid residue at the 3 position, the deacylated lipid A species of the molecular ion at m/z 1477 missing the primary 3-hydroxydecanoic acid residue at the 3 position, the deacylated lipid A species of the molecular ion at m/z 1477 missing a primary 3-hydroxytetradecanoic acid residue, and the deacylated lipid A species of the molecular ion at m/z 1477, missing both the primary 3-hydroxydecanoic acid residue at the 3 position and a primary 3-hydroxytetradecanoic acid residue, respectively. The peaks at m/z 1320, 1490, 1545, 1625, 1715, and 1796 correspond to the PagP-mediated palmitoylation of the molecular ions present at m/z 1081, 1251, 1307, 1387, 1477, and 1557, respectively.

EXAMPLES

Experimental Procedures

Bacterial Strains and Growth Conditions

All bacterial strains used in this study are described in Table I. Typically, the *E. coli* and *P. aeruginosa* strains were grown at 37° C. on modified Luria-Bertani broth agar, designated LB agar (26), or in LB broth, while shaking at 200 rpm. For *E. coli*, the medium was supplemented with 0.2% glucose. When appropriate, bacteria were grown in the presence of 100 μg/ml ampicillin, 50 μg/ml kanamycin, 50 μg/ml nalidixic acid, or 100 μg/ml streptomycin, for plasmid maintenance or strain selection. *S. Typhimurium* SR11 was grown on LB agar plates at 37° C. *B. bronchiseptica* and *B. pertussis* strains were grown at 35° C. on Borduet-Gengou agar (Difco) supplemented with 15% defibrinated sheep blood. To induce the expression of the pagL$_{(Bb)}$ gene in *B. pertussis*, the bacteria were grown in synthetic Thijs medium (48) supplemented with 1 mM isopropyl-1-thio-β-D-galactopyranoside (IPTG) (end concentration) at 35° C., while shaking (180 rpm).

TABLE 1

Bacterial strains and plasmids used in this study

| Strain or plasmid | Genotype or description | Source or reference |
|---|---|---|
| Strains | | |
| *B. bronchiseptica* | | |
| B505 | Wild-type strain | N.V.I.[a] |
| *B. pertussis* | | |
| B509 | Dutch vaccine strain | N.V.I.[a] |
| B134 | Dutch vaccine strain | N.V.I.[a] |
| Tohama | Wild-type strain Nal[R] Strep[R] | 36 |
| *P. aeruginosa* | | |
| PAO25 | PAO1 leu arg | 45 |
| *S. Typhimurium* | | |
| SR11 | Wild-type strain | 46 |
| *E. coli* | | |
| TOP10F' | F'{lacI$^q$ Tn10 (Tet$^R$)} mcrA Δ(mrr-hsdRMS-mcrBC) Φ80lacZΔM15 ΔlacX74 deoR recA1 araD139 (ara-leu)7697 galU galK rpsL endA1 nupG | Invitrogen |
| DH5α | F Δ(lacZYA-algF)U169 thi-1 hsdR17 gyrA96 recA1 endA1 supE44 relA1 phoA Φ80 dlacZΔM15 | 47 |
| BL21 Star ™ (DE3) | F ompT hsdS B (rB$^-$ mB$^-$) gal dcm rne131 (DE3) | Invitrogen |
| SK2257 | F crcA280::Tn10$^c$ thyA6 rpsL120(Str$^R$) deoC1 | CGSC[b] |
| JG101 | BL21 Star ™ (DE3) crcA280::Tn10$^c$ | This study |
| SM10 | RP4-2-Tc::Mu recA Km$^R$ | 50 |
| Plasmids | | |
| pCRII-TOPO | *E. coli* cloning vector Amp$^R$ Kan$^R$ | Invitrogen |
| pET-11a | *E. coli* high-copy expression vector, Amp$^R$, T7 promotor | Novagen |
| pMMB67EH | Broad-host-range expression vector, AmpR, tac promotor | 51 |
| pMMB67EH | Broad-host-range expression vector, AmpR, tac promotor | 51 |
| pMMB67-PagL$_{(Bb)}$ | pMMB67 derivative harboring *B. bronchiseptica* pagL | This study |
| pPagL$_{(Pa)}$ | pET-11a derivative harboring *P. aeruginosa* pagL | This study |
| pPagL$_{(Bb)}$ | pET-11a derivative harboring *B. bronchiseptica* pagL | This study |
| pPagL$_{(St)}$ | pET-11a derivative harboring *S. Typhimurium* pagL | This study |
| pPagL$_{(Pa)}$(—) | pET-11a derivative encoding *P. aeruginosa* pagL without signal sequence | This study |
| pPagL$_{(Pa)(H81A)}$ | pPagL$_{(Pa)}$ encoding PagL$_{(Pa)}$ with H81A substitution | This study |
| pPagL$_{(Pa)(H81N)}$ | pPagL$_{(Pa)}$ encoding PagL$_{(Pa)}$ with H81N substitution | This study |
| pPagL$_{(Pa)(S84A)}$ | pPagL$_{(Pa)}$ encoding PagL$_{(Pa)}$ with S84A substitution | This study |
| pPagL$_{(Pa)(S84C)}$ | pPagL$_{(Pa)}$ encoding PagL$_{(Pa)}$ with S84C substitution | This study |
| pPagL$_{(Pa)(H149A)}$ | pPagL$_{(Pa)}$ encoding PagL$_{(Pa)}$ with H149A substitution | This study |
| pPagL$_{(Pa)(H149N)}$ | pPagL$_{(Pa)}$ encoding PagL$_{(Pa)}$ with H149N substitution | This study |
| pPagL$_{(Pa)(S151A)}$ | pPagL$_{(Pa)}$ encoding PagL$_{(Pa)}$ with S151A substitution | This study |
| pPagL$_{(Pa)(S151C)}$ | pPagL$_{(Pa)}$ encoding PagL$_{(Pa)}$ with S151C substitution | This study |

[a]Netherlands Vaccine Institute, Bilthoven, The Netherlands
[b]*E. coli* genetic stock center, Yale university, New Haven (CT)
[c]pagP is also known as crcA Recombinant DNA Techniques Plasmid DNA was isolated using the Promega Wizard®Plus SV Minipreps system. Calf-intestine alkaline phosphatase and restriction endonucleases were used according to the instructions of the manufacturer (Fermentas). DNA fragments were isolated from agarose gels using the Qiagen quick gel extraction kit. Ligations were performed by using the rapid DNA ligation kit (Roche).

The pagL genes from *S. Typhimurium* SR11 (pagL$_{(St)}$), *B. bronchiseptica* B505 (pagL$_{(Bb)}$), and the pagL gene, with or without its signal sequence-encoding part, from *P. aeruginosa* PAO25 (pagL$_{(Pa)}$, pagL$_{(Pa)}$(−)) were cloned into pET-11a (Novagen) behind the T7 promoter. The genes were amplified by PCR using chromosomal DNA as template. Template DNA was prepared by resuspending ~10$^9$ bacteria in 50 μl distilled water, after which the suspension was heated for 15 min at 95° C. The suspension was then centrifuged for 1 min at 16,100×g, after which the supernatant was used as template DNA. The sequences of the forward primers, which contained an NdeI site (underlined), including an ATG start codon, were 5'-AA<u>CATATG</u>AAGAGAATATTTATATATC-3' (pagL$_{(St)}$), SEQ ID NO:18
5'-AA<u>CATATG</u>AAGAAACTACTTCCGCTGG-3' (pagL$_{(Pa)}$), SEQ ID. NO:19
5'-AA<u>CATATG</u>GCGGACGTCTCGGCCGCCG-3' (pagL$_{(Pa)}$(−)), SEQ ID NO:20 and
5'-AA<u>CATATG</u>CAATTTCTCAAGAAAAACA-3' (pagL$_{(Bb)}$). SEQ ID NO:21

The sequences of the reverse primers, which contained an BamHI site (underlined) and included a stop codon, were
5'-AA<u>GGATCC</u>TCAGAAATTATAACTAATT-3' (pagL$_{(St)}$), SEQ ID NO:22
5'-AA<u>GGATCC</u>CTAGATCGGGATCTTGTAG-3' (pagL$_{(Pa)}$, pagL$_{(Pa)}$(−)), SEQ ID NO:23 and
5'-AA<u>GGATCC</u>TCAGAACTGGTACGTATAG-3' (pagL$_{(Bb)}$). SEQ ID NO:24

The PCRs were done under the following conditions: 50 μl total reaction volume, 25 pmol of each primer, 0.2 mM dNTPs, 3 µl template DNA solution, 1.5% dimethylsulfoxide, 1.75 units of Expand High Fidelity enzyme mix with buffer supplied by the manufacturer (Roche). The temperature program was as follows: 95° C. for 3 min, a cycle of 1 min at 95° C., 1 min at 60° C., and 1 min 30 s at 72° C. repeated 30 times, followed by 10 min at 72° C. and subsequent cooling to 4° C. The PCR products were purified from agarose gel and subsequently cloned into pCRII-TOPO. Plasmid DNA from correct clones was digested with NdeI and BamHI, and the PagL-encoding fragments were ligated into NdeI/BamHI-digested pET-11a. The ligation-mixture was used to transform $E.$ $coli$ DH5α using the $CaCl_2$ method (27). Plasmid DNA from transformants was checked for presence of the correct PagL-encoding insert by digestion with NdeI and BamHI. Plasmids that gave a correct digestion profile were designated pPagL$_{(Pa)}$, pPagL$_{(Pa)}$(-), pPagL$_{(Bb)}$, and pPagL$_{(St)}$ (Table I). The correct coding sequences of the cloned pagL genes were confirmed by nucleotide sequencing in both directions. To subclone the pagL$_{(Bb)}$ gene into the broad-host-range, low-copy pMMB67EH vector, pPagL$_{(Bb)}$ plasmid DNA was digested with XbaI and HinDIII, and the PagL$_{(Bb)}$-encoding fragment was ligated into XbaI/HinDIII-digested pMMB67EH. The ligation mixture was used to transform $E.$ $coli$ DH5α. Plasmid DNA from transformants was checked for presence of the correct PagL-encoding insert by digestion with XbaI and HinDIII. A plasmid that gave a correct digestion profile was designated pMMB67EH-PagL$_{(Bb)}$ (Table I). The latter plasmid was used to transform $E.$ $coli$ SM10, which allowed subsequent transfer of pMMB67EH-PagL$_{(Bb)}$ to $B.$ $pertussis$ by conjugation on solid medium as described by Stibitz et al. (52). Mutations were introduced in pagL by using the QuikChange® Site-Directed Mutagenesis Kit (Stratagene) and the primers listed in Table II. Plasmid pPagL$_{(Pa)}$ was used as the template in which the mutations were created. The presence of the correct mutations was confirmed by nucleotide sequencing in both directions.

TABLE II

Primers used for site-directed mutagenesis

| Name[a] | Sequence (5'-3')[b] | SEQ ID NO: |
|---|---|---|
| H81A_FW | GAAGGCGCCGGCAAG<u>GCG</u>TCGCTGTCGTTCGCT | 25 |
| H81A_REV | AGCGAACGACAGCGA<u>CGC</u>CTTGCCGGCGCCTTC | 26 |
| H81N_FW | GAAGGCGCCGGCAAG<u>AAC</u>TCGCTGTCGTTCGCT | 27 |
| H81N_REV | AGCGAACGACAGCGA<u>GTT</u>CTTGCCGGCGCCTTC | 28 |
| S84A_FW | GGCAAGCATTCGCTG<u>GCG</u>TTCGCTCCGGTATTC | 29 |
| S84A_REV | GAATACCGGAGCGAA<u>CGC</u>CAGCGAATGCTTGCC | 30 |
| S84C_FW | GGCAAGCATTCGCTG<u>TGC</u>TTCGCTCCGGTATTC | 31 |
| S84C_REV | GAATACCGGAGCGAA<u>GCA</u>CAGCGAATGCTTGCC | 32 |
| H149A_FW | GGCGTTCGGGCGATC<u>GCG</u>TATTCCAACGCCGGC | 33 |
| H149A_REV | GCCGGCGTTGGAATA<u>CGC</u>GATCGCCCGAACGCC | 34 |
| H149N_FW | GGCGTTCGGGCGATC<u>AAC</u>TATTCCAACGCCGGC | 35 |
| H149N_REV | GCCGGCGTTGGAATA<u>GTT</u>GATCGCCCGAACGCC | 36 |
| S151A_FW | CGGGCGATCCACTAT<u>GCG</u>AACGCCGGCCTGAAA | 37 |
| S151A_REV | TTTCAGGCCGGCGTT<u>CGC</u>ATAGTGGATCGCCCG | 38 |
| S151C_FW | CGGGCGATCCACTAT<u>TGC</u>AACGCCGGCCTGAAA | 39 |
| S151C_REV | TTTCAGGCCGGCGTT<u>GCA</u>ATAGTGGATCGCCCG | 40 |

[a]The primer name gives the amino acid substitution, e.g. H81A_FW indicates that the oligonucleotide shown was used as the forward primer in a site-directed mutagenesis procedure to substitute the histidine at position 81 of the precursor PagL$_{(Pa)}$ by an alanine.
[b]Introduced mutations are underlined.

SDS-PAGE and Immunoblotting

Proteins were analyzed by sodium dodecyl sulfate-polyacrylamide gel electrophoresis (SDS-PAGE) (28), with 0.2% SDS in the running gel, by using the Bio-Rad Mini-PROTEAN®3 apparatus. Samples were applied to a 13% polyacrylamide gel with a 4% stacking gel and subjected to electrophoresis at 150 V. Proteins were stained with Coomassie Brilliant Blue. Prestained or unstained Precision Plus Protein™ Standard from Bio-Rad was used to determine the relative molecular mass ($M_r$). For Western blotting, proteins were transferred from SDS-PAGE gels onto nitrocellulose membranes. The membranes were blocked overnight in phosphate-buffered saline (PBS) (pH 7.6), 0.5% non-fat dried milk, 0.1% Tween-20 and incubated with primary antibodies directed against PagL$_{(Pa)}$ in blocking buffer, followed by an incubation with horse-radish peroxidase-conjugated rabbit anti-guinea pig IgG antibodies (Sigma) in blocking buffer. Blots were developed using SuperSignal® WestPico Chemiluminescent Substrate (Pierce).

Semi-Native SDS-PAGE

Proteins were analysed by sodium dodecyl sulfate-polyacrylamide gel electrophoresis (SDS-PAGE) (28), with 0.2% SDS in the running gel, by using the Bio-Rad Mini-PROTEAN®3 apparatus. For semi-native SDS-PAGE, no SDS was added to the running and stacking gel, and the samples were not heated prior to electrophoresis. Samples were applied to a 13% polyacrylamide gel with a 4% stacking gel and subjected to electrophoresis at 150 V. For semi-native SDS-PAGE, electrophoresis was performed at a constant current of 15 mA on ice. Proteins were stained with Coomassie Brilliant Blue. Prestained or unstained Precision Plus Protein™ Standard from Bio-Rad was used to determine the relative molecular mass ($M_r$).

Tricine-SDS-PAGE

To LPS-containing samples 0.5 mg/ml proteinase K (end concentration) was added to the sample buffer (28). The samples were incubated for 60 min at 55° C., followed by 10 min at 95° C. to inactivate proteinase K. The samples was then diluted 10 fold by adding sample buffer, after which 2 µl of the sample were applied to a Tricine-SDS-PAGE gel (30). The bromophenol blue was allowed to run into the separating gel at 35 V, after which the voltage was increased to 105 V. After the front reached the bottom of the gel, the samples were left running for another 45 min. The gels were fixed overnight in water/ethanol/acetic acid 11:8:1 (v/v/v) and subsequently stained with silver as described (31).

Polyclonal Antibodies

For antibody production, pPagL$_{(Pa)}$(-), was used to transform $E.$ $coli$ BL21 Star™ (DE3) to allow for expression of the truncated pagL gene. The PagL$_{(Pa)}$ protein, accumulating in inclusion bodies, was isolated (29), purified from a preparative SDS-PAGE gel, and used for immunization of guinea pigs at Eurogentec.

Microsequencing

Proteins were transferred from SDS-PAGE gels to an Immobilon™-P polyvinylidene difluoride membrane (Millipore Corp.) in 192 mM glycine, 25 mM Tris (pH 8.3), 10% methanol (v/v) at 100 V for 1 h using the Bio-Rad Mini-PROTEAN®2 blotting apparatus. After transfer, the membrane was washed 3 times for 15 min with distilled water. Transferred proteins were stained with Coomassie Brilliant Blue. The membrane was dried in the air, and the putative PagL bands were excised and subjected to microsequencing at the Sequencing Center Facility, Utrecht University, the Netherlands.

Isolation of LPS and Analysis by Gas Chromatography-Mass Spectrometry (GC/MS)

LPS was isolated using the hot phenol/water extraction method (3). In short, B. pertussis strain Tohama, with or without plasmid pMMB67EH-PagL$_{(Bb)}$, was grown in 3 liters Thijs medium (48) in the presence of 1 mM IPTG (end concentration). Cells were harvested by centrifugation and resuspended in 40 mM sodiumphosphate buffer (pH 7.0) containing 5 mM EDTA. The cells were treated over night with lysozyme at 4° C., after which an equal volume of phenol was added. The suspension was heated to 70° C. and incubated for 30 minutes while shaking. The suspension was cooled to 10° C., after which phases were separated by centrifugation. The upper phase was collected and the extraction was repeated by adding an equal volume of distilled water to the lower phase. After subsequent incubation at 70° C., cooling, and centrifugation, the two upper phases were mixed and dialysed against tap water until the phenol odour disappeared. After freeze-drying the dialysed fractions, LPS was dissolved in phosphate-buffered saline (pH 7.2) at a concentration of 1 mg/ml. For fatty acid analysis by GC/MS, a five-fold (v/v) excess of acetone was added to an aliquot of the isolated LPS, after which the solution was dried at 60° C. under a nitrogen flow. Subsequently, 10 µg of C12:0(2OH) (1 mg/ml in ethanol) was added as an internal standard, as well as 100 µl of acetylchloride/ethanol 1:9 (v/v), after which the samples were derivatized for 1 h at 90° C. After cooling, the reaction was stopped by adding 200 µl of 1 M $K_2HPO_4$ (pH 8.0), followed by extraction of the acyl-ethyl esters with 200 µl ethyl acetate. A 1-µl volume of the upper phase was used for analysis by GC/MS on a Finnigan MAT SSQ in the electron-impact mode.

Biological Activity of LPS

IL-6 and IL-10 induction by wild type and PagL-modified B. pertussis Tohama LPS was tested with the human macrophage cell line MM6 (49). MM6 cells were seeded in microtiter plates (2·10$^5$/well) in 400 µl of IMDM (Gibco BRL) supplemented with 10% fetal calf serum (Gibco BRL) and stimulated with 200 µl of serial dilutions of the LPS stock solution, for 16-18 h at 37° C. in a humid atmosphere containing 5% $CO_2$. IL-6 and IL-10 levels in the culture supernatants were quantified with an ELISA against human IL-6 or IL-10 according to the instructions of the manufacturer (Peli-Pair™ reagent set, Sanquin Reagents, Amsterdam, The Netherlands).

Isolation of Cell Envelopes

Cells were harvested by centrifugation for 10 min at 1,500×g, and washed once in 50 ml of cold 0.9% sodium chloride solution. The cell pellets were frozen for at least 15 min at −80° C., and then suspended in 20 ml of 3 mM EDTA, 10 mM Tris-HCl (pH 8.0) containing Complete Protease inhibitor cocktail (Roche). The cells were disrupted by sonication, after which unbroken cells were removed by centrifugation for 10 min at 1,500×g. The cell envelopes were pelleted from the supernatant by centrifugation for 1.5 h at 150,000×g and resuspended in 2 mM Tris-HCl (pH 7.4). The cell envelopes were stored at −80° C. in aliquots.

Isolation of Inclusion Bodies

For inclusion body isolation, PagL$_{(Pa)}$(−) was expressed in E. coli BL21 Star™ (DE3) from pPagL$_{(Pa)}$(−) (Table 1). A Two-liter culture was grown at 37° C. in LB medium supplemented with ampicillin till an OD$_{600}$ between 0.4 and 0.6. Then, 1 mM IPTG (end concentration) was added to the culture to induce expression of the recombinant gene, after which the culture was incubated further at 37° C., while shaking. After approximately 4 hours, cells were harvested by centrifugation (15 min at 4,000 rpm (4° C.)). Harvested cells were washed once in 400 ml 0.9% NaCl and then resuspended in 80 ml TE 50:40 (50 mM Tris-HCl (pH 8.0), 40 mM EDTA). Sucrose (0.25 g/ml (end concentration)) and lysozyme (0.2 mg/ml (end concentration)) were added, after which the suspension was incubated for 30 min at RT, while shaking. The suspension was sonicated three times on ice (1.5 min, with 2 min pauses in-between) using a Branson 250 Sonfier with macrotip (output 9, duty cycle 50%). Following sonication, 0.13% (w/v) Brij-35P (Fluka) was added, and the suspension was sonicated for an additional 2 min. Dense material (inclusion bodies) was collected by centrifugation for 2 hrs at 4,000 rpm (4° C.), after which the pellet was washed once in 40 ml TE 50:40, followed by another washing step using 40 ml 10 mM Tris-HCl (pH 8.3). The obtained inclusion bodies were solubilized in 8 M urea supplemented with 10 mM glycine (pH 8.3) and precipitated with TCA. Finally, the obtained proteins were solubilized in 8 M urea supplemented with 10 mM glycine (pH 8.3) at a protein concentration of 10 mg/ml. This mixture was centrifugated for 2 hrs at 13,000 rpm to remove residual insoluble material and membranes.

Refolding and Purification of PagL$_{(Pa)}$(−)

PagL$_{(Pa)}$(−) was refolded in vitro by two-fold dilution of the 10 mg/ml protein solution (see above) in 10% (w/v) lauryldimethylamine oxide (LDAO) and subsequent sonication for 10 min. Refolded PagL$_{(Pa)}$(−) was purified by Fast Protein Liquid Chromatography (FPLC) using a 1 ml MonoQ (Amersham Biosciences) ion-exchange column. The protein solution was diluted 4 times in buffer A (20 mM Tris-HCl (pH 8.0), 0.08% (w/v) $C_{10}E_5$). The solution was loaded onto the column, which was pre-equilibrated with buffer A, and washed once with buffer A, and the proteins were eluted with a linear gradient of 0-1 M NaCl in buffer A. Fractions were analysed by SDS-PAGE for the presence of the refolded PagL$_{(Pa)}$(−) protein. Those containing the protein were pooled and concentrated to a protein concentration of 10 mg/ml using Centricon concentrators with a molecular mass cut-off of 3 kDa (Amicon). The protein solution was then dialyzed three times overnight against 10 ml 2 mM Tris-HCl (pH 8.0), 0.06% (w/v) $C_{10}E_5$ using a membrane with a molecular mass cut-off of 3.5 kDa.

In Vitro Modification Assay

Refolded PagL$_{(Pa)}$(−) (10 mg/ml) or cell envelopes isolated from E. coli BL21 Star™ (DE3) containing the empty vector pET-11a or the pPagL plasmids were diluted 10 fold in double distilled water. 4 µl of the diluted refolded protein or cell envelope solution was incubated in 50 mM Hepes (pH 8.0), 0.1% Triton X-100, 0.5 M NaCl, and 0.75 nmol N. meningitidis L3-LPS in a final volume of 10 µl at 37° C. for 16 h. To test whether the reaction was dependent on divalent cations, 5 mM EDTA was added into the reaction with the refolded PagL$_{(Pa)}$(−). The reactions were terminated by boiling in sample buffer (28), after which the samples were treated with 0.5 mg/ml proteinase K for 1 hour at 55° C., followed by 10 min incubation at 95° C. The samples were diluted 25 fold by adding sample buffer, after which 2 µl of the samples were analysed by Tricine-SDS-PAGE (see above).

Isolation of LPS and Analysis by Electrospray Ionisation-Mass Spectrometry (ESI-MS)

LPS was isolated using the hot phenol/water extraction method (Westphal and Jann, Methods Carbohydr. Chem. 5; 83-91, 1965) with slight modifications. In short, bacteria were grown in THIJS medium in the presence of 1 mM IPTG (end concentration) for 64 h. Cells were harvested by centrifugation and resuspended in 40 mM sodium phosphate buffer (pH 7.0) containing 5 mM EDTA. The cells were treated overnight with lysozyme at 4° C., after which an equal volume of phenol was added. The suspension was heated to 70° C., incubated for 30 min while shaking, and subsequently cooled to 10° C., after which phases were separated by centrifugation for 10 min at 8,000×g. The upper phase was collected and the extraction was repeated after adding an equal volume of distilled water to the lower phase. The two upper phases were combined, dialysed against tap water until the phenol odour disappeared, freeze-dried, and subsequently taken up in distilled water. The LPS was subsequently pelleted by centrifugation for 3 h at 150,000×g and dissolved in distilled water, after which the LPS concentration was determined by analysing the 3-hydroxytetradecanoic acid content, using a 6890 Agilent gas chromatograph, as described (Welch, Clin. Microbiol. Rev. 1991). For ESI-MS, a 200 µl aliquot of isolated LPS (50 nmol/ml) was freeze-dried and taken up in 0.1 ml 2% acetic acid. The mixture was heated for 2 h at 95° C. to hydrolyse the LPS and release the lipid A moiety. Subsequently, the mixture was cooled to room temperature and centrifuged for 10 min at 16,100×g. The pellet was washed twice in 0.1 ml double-distilled water, taken up in 0.1 ml double-distilled water, and 0.3 ml chloroform/methanol (2:1, v/v) was added. After vigorous vortexing, phases were separated by centrifugation for 10 min at 16,100×g. The upper phase was then used for structural analysis of purified lipid A by nanoelectrospray tandem MS on a Finnigan LCQ in the negative ion mode (Wilm and Mann, Anal. Chem. 1996).

Example 1

Identification of PagL Homologs in Various Gram-Negative Bacteria

The 187-amino acid sequence of the S. Typhimurium PagL precursor protein (GenBank Accession Number AAL21147, SEQ ID No:17) was used as a lead to identify putative PagL homologs in other Gram-negative bacteria, by searching all completed and unfinished genomes of Gram-negative bacteria present in the NCBI database World wide Web URL ncbi.nlm.nih.gov/sutils/genom_table.cgi). BLAST search (34) revealed the presence of putative homologs in the Bordetella spp. B. pertussis, B. bronchiseptica, and B. parapertussis (FIG. 2). The PagL homologs of B. bronchiseptica and B. parapertussis are two mutually identical 178-amino acid polypeptides (FIG. 2) with, as predicted by the signalP server (35), a 25-amino acid N-terminal signal peptide. A gene for a PagL homolog was also found in the genome of the B. pertussis Tohama I strain (36), but this open reading frame. (ORF) was disrupted by a frame shift (SEQ ID No:4), which could be restored as in SEQ ID No:5 to encode a protein as in SEQ ID No:1. Nucleotide sequencing of the PagL ORFs from B. pertussis strains B509 and B134 also showed the presence of the same frame shift[2], which indicates that disruption of the PagL ORF might be a common feature in B. pertussis strains. By using the newly identified B. bronchiseptica PagL homolog as a probe for further BLAST analysis, additional putative pagL homologs could be identified in the genomes of P. aeruginosa (SEQ ID No:6, 30% identity), Pseudomonas fluorescens (SEQ ID No:7, 29% identity), Pseudomonas syringae (SEQ ID No:8, 31% identity), Pseudomonas putida, 2× (SEQ ID No:9+10, 32/33%), Ralstonia metallidurans (SEQ ID No:15, 28%), Ralstonia solanacearum (SEQ ID No:16, 29%), Burkholderia mallei (SEQ ID No:12, 28%), Burkholderia pseudomallei (SEQ ID No:13, 28%), Burkholderia fungorum (SEQ ID No:11, 29%), and Azotobacter vinelandii (SEQ ID No:14, 27%) Alignments are shown in FIG. 2. Together, all PagL homologs exhibited a low overall mutual sequence identity, albeit higher than with S. typhimurium (24% identity), but contained a clear homologous domain near the C terminus. Our finding of this conserved motif allows identification of PagL homologs in other (bacterial) species and allows the use of a suitable PagL homolog for any host bacterium and/or any LPS to be 3-O-deacylated.

Example 2

Cloning of pagL and Heterologous Expression in E. coli

To verify their putative lipid A-deacylase activity, we cloned the pagL homologs of P. aeruginosa ($pagL_{(Pa)}$) and B. bronchiseptica ($pagL_{(Bb)}$). We included in these studies $pagL_{(St)}$ as a reference. These pagL genes were amplified from the chromosomes by PCR and eventually cloned in pET-11a under the control of the T7 promoter, resulting in plasmids, $pPagL_{(Pa)}$, $pPagL_{(Bb)}$, and $pPagL_{(St)}$.

To investigate expression and membrane localization of PagL in E. coli, E. coli BL21 Star™ (DE3) containing the empty vector pET-11a or the pPagL plasmids were grown overnight in LB, after which cell envelopes were isolated. Analysis by SDS-PAGE revealed the presence of prominent additional bands with $M_r$s of 15000-18000 in the cell envelopes of the cells expressing PagL (FIG. 3). This was consistent with the expected molecular masses of the mature PagL proteins, i.e. $PagL_{(Pa)}$ 16.1 kDa, $PagL_{(Bb)}$ 17.2 kDa, and $PagL_{(St)}$ 18.2 kDa. To identify the additional protein bands, they were subjected to microsequencing. The sequences of the first 5 amino acid residues of $PagL_{(Pa)}$, $PagL_{(Bb)}$, and $PagL_{(St)}$ were ADVSA, QPTQG, and NDNVF, respectively, indicating that cleavage of the signal peptide by leader peptidase occurs between amino acid residues 23 and 24 (AQA-ADV), 25 and 26 (AQA-QPT), and between 20 and 21 (CSA-NDN), respectively. Particularly in the case of expression of $PagL_{(Bb)}$, an additional band with a higher $M_r$ was visible on the gel (FIG. 2). The N-terminal sequence of this band, MQFLK, corresponded with that of the precursor of $PagL_{(Bb)}$.

Example 3

In vivo Modification of E. coli LPS by PagL

To study whether the cloned PagL homologs were active on E. coli LPS, IPTG was added to exponentially growing E. coli BL21 Star™ (DE3) cells containing the empty vector pET-11a or the pPagL plasmids, and after various incubation periods, samples equivalent to one $OD_{600}$ unit were collected and their LPS content was analyzed by Tricine-SDS-PAGE. In accordance with the expected hydrolysis of the R-3-hydroxy-myristate at the 3 position of lipid A, expression of any of the three pagL homologs converted the LPS into a form with a higher electrophoretic mobility (FIG. 4). The conversion was almost complete within 75 min after PagL$_{(Pa)}$ or PagL$_{(Bb)}$ were induced, but took somewhat longer in the case of PagL$_{(St)}$.

Figure 6A:
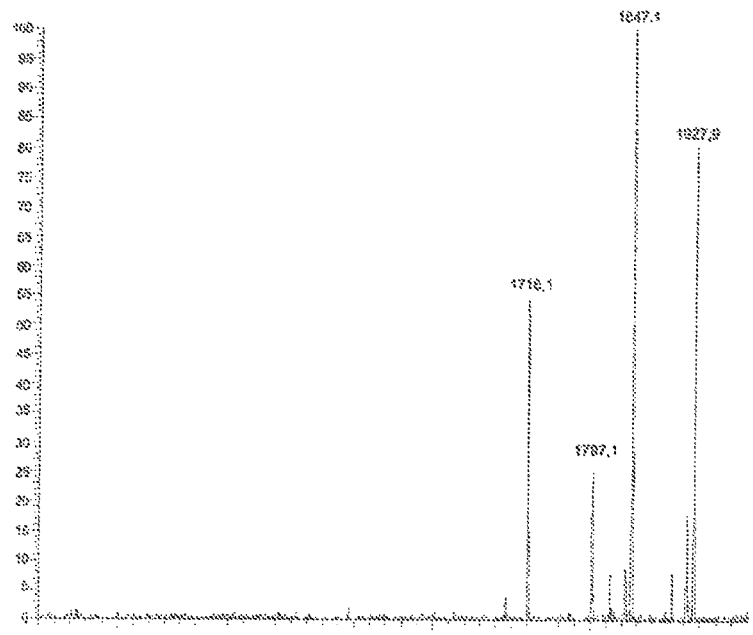
Figure 6B:
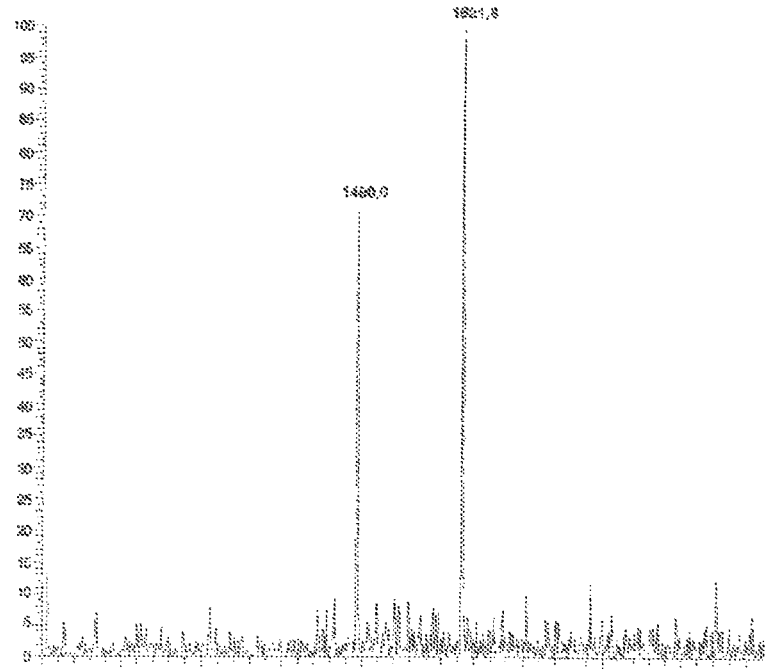
Figures 6C, 6D:
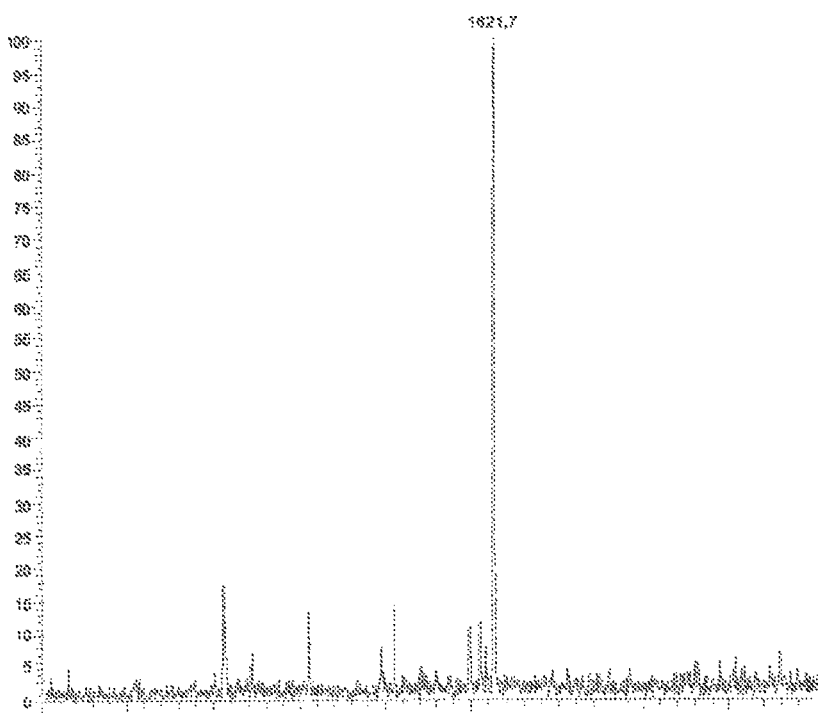

Structural Analysis of PagL-Modified LPS: to determine its fatty acid content, LPS was isolated from bacteria that were grown in the presence of 10 mM MgCl$_2$ to suppress PhoP/PhoQ-regulated modifications of lipid A and analyzed by GC/MS. The C14:0/C14:0(3OH) ratio in the PagL-modified LPS samples was increased as compared with that in the wild-type LPS (FIG. 5), consistent with the expected removal of a C14-3OH from lipid A. To confirm these data, the lipid A moieties were isolated and analyzed by ESI-MS in the positive ion mode, which revealed the presence of four major lipid A species in wild-type LPS (FIG. 6A). The peak at m/z 1797 represents the characteristic hexa-acylated bis-phosphate species that is typically found in E. coli, whereas the peak at m/z 1928 corresponds to a hexa-acylated bis-phosphate species substituted with an L-Ara4N moiety. The two remaining peaks at m/z 1716 and m/z 1847 most likely represent fragment ions of the two former species missing a phosphate group. Upon expression of PagL$_{(St)}$ (FIG. 6B), PagL$_{(Pa)}$ (FIG. 6C), or PagL$_{(Bb)}$ (FIG. 6D), the major lipid A species were present at m/z 1622 and m/z 1490, which correspond to the loss of one β-hydroxymyristate residue and one phosphate group from the major species at m/z 1928 and m/z 1797 present in the empty vector control, respectively. Also here, the loss of the phosphate group is probably an artefact of the ionisation procedure. Based upon the GC/MS and ESI-MS data, it can be concluded that the identified PagL homologs of P. aeruginosa and B. bronchiseptica, like that of S. Typhimurium, are active lipid A deacylases. Furthermore, the data suggest that the deacylation is not dependent upon the absence or presence of an L-Ara4N moiety, since both species were deacylated efficiently.

Example 4

Subsequent In Vivo Modification of PagL-Deacylated LPS

In the course of these experiments, it was observed that after prolonged PagL expression, PagL-modified LPS was no longer detectable on Tricine-SDS-PAGE gels, and that the LPS migrated again at the position of wild-type LPS, as illustrated for the strain expressing PagL$_{(Bb)}$ (FIG. 7A). The PagL protein was still abundantly present at this time point, as revealed on SDS-PAGE gels (data not shown). Furthermore, analysis by GC/MS revealed that the C14:0/C14:0(3OH) ratio was not decreased again for the LPS isolated after 5 h induction of PagL$_{(Bb)}$ (FIG. 7B). Thus, the secondary modification observed on the Tricine-SDS-PAGE gel (FIG. 7A) was not the consequence of restoration of the PagL modification, but the result of (an) additional modification(s) that restored the electrophoretic mobility to that of wild-type LPS. Therefore, other fatty acid ratios were compared. A striking increase in the C16:0/C14:0 ratio was found in the LPS of cells induced 5 h for PagL production (FIG. 7C), suggesting that the PagL-deacylated LPS was subsequently palmitoylated.

A protein that adds palmitate to lipid A is the outer membrane protein PagP (19) (FIG. 1). Therefore, we hypothesized that the secondary modification of PagL-modified LPS might have been the result of endogenous PagP activity. To investigate this possibility, we transformed wild-type E. coli BL21 Star™ (DE3) and its pagP mutant derivative JG101 with the pPagL$_{(Pa)}$ plasmid. The secondary modification of PagL-modified LPS was again observed in the case of the wild-type strain, but not in that of the mutant strain (FIG. 7D). This result strongly suggests that the secondary modification of PagL-modified LPS (FIG. 7A) was indeed the consequence of endogenous PagP activity.

Example 5

Identification of PagL Active-Site Residues

Figure 9A:
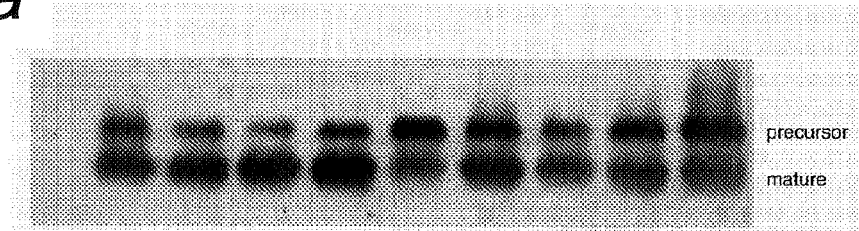
Figure 9B:
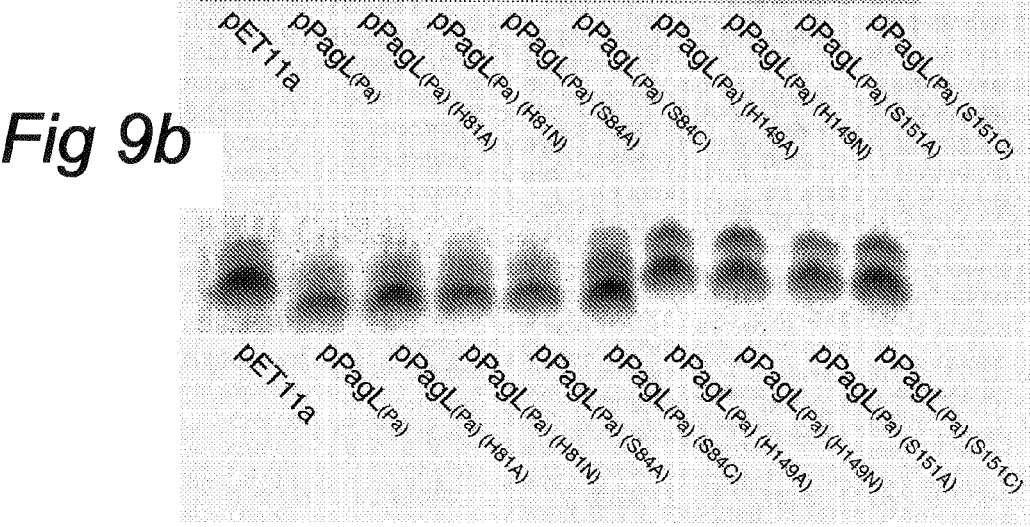

The mutual sequence identity between the identified PagL homologs is very low (FIG. 2). Among the few totally conserved residues are a histidine and a serine, which, we hypothesize, might be part of a 'classical' Asp/Glu-His-Ser catalytic triad of serine hydrolases. These putative active-site residues are located at the lipid-exposed side near the top of a β-strand in a topology model we propose (FIG. 8). Interestingly, in the outer membrane phospholipase A, the active-site His and Ser are located in a similar position (37). To test whether these residues, located at positions 149 and 151 of the PagL$_{(Pa)}$ precursor protein, respectively, are indeed important for catalytic activity, they were substituted by alanine or asparagine, and by alanine or cysteine, respectively. As a control, the same substitutions were made for a non-conserved histidine and serine residue, located at positions 81 and 84 of the PagL$_{(Pa)}$ precursor, respectively. The protein and LPS profiles of E. coli BL21 Star™ (DE3) cells carrying the relevant plasmids and induced for 75 min with IPTG were analyzed by immunoblotting (FIG. 9A) and Tricine-SDS-PAGE (FIG. 9B), respectively. Whereas substitution of the non-conserved His81 and Ser84 did not affect LPS deacylation, deacylation of LPS was no longer observed when the conserved His149 and Ser151 were substituted (FIG. 9B), even though the expression of these mutant proteins was not affected (FIG. 9A). These results strongly support the hypothesis that the conserved histidine at position 149 and serine at position 151 of the precursor PagL$_{(Pa)}$ protein are active-site residues and that PagL mechanistically functions as a serine hydrolase.

Example 6

Cloning of pagL$_{(Bb)}$ and Heterologous Expression in B. pertussis

To modify B. pertussis LPS in vivo, we cloned the pagL gene of B. bronchiseptica (pagL$_{(Bb)}$). The pagL gene was amplified from the chromosome by PCR and eventually cloned in pMMB67EH under the control of the Tac promoter, resulting in plasmid, pMMB67EH-$PagL_{(Bb)}$, which was transferred to *B. pertussis* strain Tohama by conjugation.

To address the modification of *B. pertussis* LPS in vivo, wild-type *B. pertussis* strain Tohama, or *B. pertussis* strain Tohama containing the pMMB67EH-$PagL_{(Bb)}$ plasmid were grown in Thijs medium supplemented with 1 mM IPTG (end concentration). LPS was isolated by the hot phenol-water extraction method and analysed by Tricine-SDS-PAGE (FIG. 10A) and GC-MS (FIG. 10B). Analysis on Tricine-SDS-PAGE gel showed that the LPS isolated from the $PagL_{(Bb)}$ expressing strain migrated slightly faster as compared to the wild type *B. pertussis* LPS. Strikingly, the LPS isolated from the $PagL_{(Bb)}$ expressing strain showed two distinct LPS populations. One population migrating around the height of the wild type Tohama LPS, and one population migrating faster. This latter LPS population can also be seen in the wild type LPS preparation, however the abundance of it is much lower. To verify that the LPS from the PagL expressing strain was indeed deacylated at its 3 position, it was analysed by GC-MS. The C14:0(3OH)/C10:0(3OH) ratio in the PagL-modified LPS sample was increased as compared with that in the wild-type LPS (FIG. 10B), consistent with the expected removal of a C10-3OH from the 3 position of *B. pertussis* lipid A.

Example 7

Biological Activity of PagL-Modified LPS

To assess the endotoxic activity of the PagL-modified and wild-type *B. pertussis* LPS, their ability to stimulate the production of IL-6 and IL-10 in the human macrophage cell line MM6 was measured. As can be seen in FIG. 2, for wild-type LPS, the production of both IL-6 (FIG. 11A) and IL-10 (FIG. 11B) by the MM6 cells is increased as compared to when the cells were stimulated with an equal amount of PagL-modified LPS. Thus, it can be concluded that the in vivo deacylation of *B. pertussis* LPS by PagL results in a reduction in endotoxic activity of this LPS.

Example 8

Cloning, Expression, Purification, and Refolding of PagL$_{(Pa)}$

The pagL gene from *P. aeruginosa* PAO25 without its signal sequence-encoding part was cloned into pET-11a, resulting in plasmid pPagL$_{(Pa)}$(−). To obtain inclusion bodies, PagL without its signal sequence was expressed in *E. coli* BL21 Star™ (DE3). Inclusion bodies were isolated and solubilized in urea, after which the protein was refolded by diluting two-fold in 10% lauryldimethylamine oxide (LDAO) and further purified by Fast Protein Liquid Chromatography (FPLC). Correct refolding was confirmed by SDS-PAGE (FIG. 12) and circular dichroism (CD) measurements (data not shown). On SDS-PAGE gel, the refolded protein had a lower electrophoretic mobility as compared to the denatured form, whereas CD measurements showed that the refolded protein predominantly had a β-sheet conformation.

Example 9

In Vitro LPS Modification by Membrane-Localized and Refolded PagL

Figure 13A:
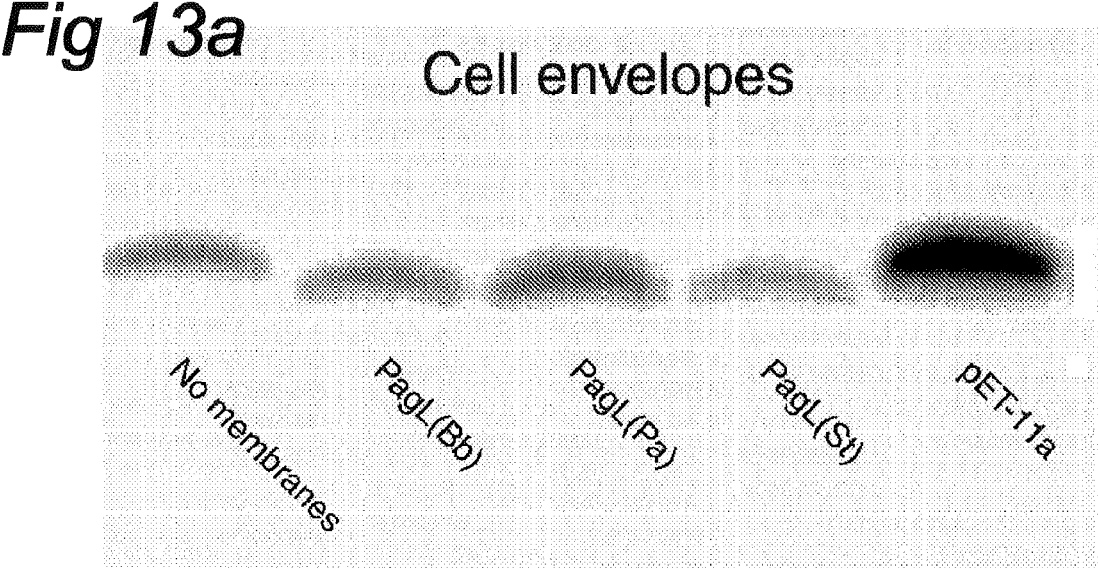
Figure 13B:
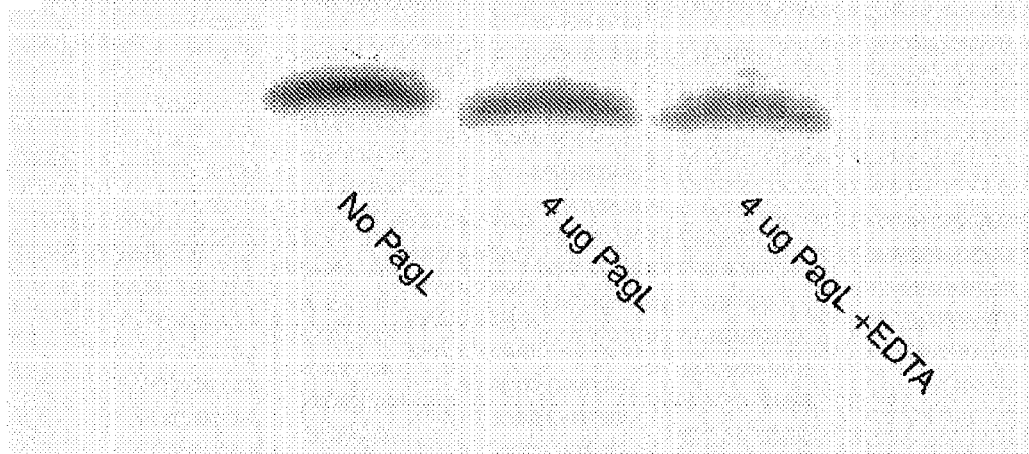

To test whether membrane-localized or in vitro refolded PagL was capable of modifying externally added LPS in vitro, we incubated refolded PagL$_{(Pa)}$(−), or isolated cell envelopes from *E. coli* BL21 Star™ (DE3) containing the empty vector pET-11a, or the pPagL plasmids, together with purified LPS of *N. meningitidis*. Modification of LPS was assessed by Tricine-SDS-PAGE (FIG. 13). In accordance with the expected hydrolysis of the R-3-hydroxymyristate at the 3 position of lipid A, LPS was converted into a form with a higher electrophoretic mobility when membrane-localized PagL (FIG. 13A) or refolded PagL$_{(Pa)}$(−) (FIG. 13B) was present. The reaction with the refolded PagL$_{(Pa)}$(−) was independent on the presence of divalent cations, as deacylation of LPS was still observed in the presence of 5 mM EDTA (FIG. 13B).

Example 10

Altered Lipid A Structure after Expression of PagP and PagL in *B. pertussis*

To express PagP and PagL in *B. pertussis* strain Tohama, the pagL gene of *B. bronchiseptica* (pagL$_{(Bb)}$) and the pagP gene of *B. pertussis* (pagP$_{(Bp)}$) were expressed from the broad-host range low-copy number expression vector pMMB67EH. As a control, a strain expressing the pagP gene of *E. coli* (pagP$_{(Ec)}$) was also constructed. LPS was isolated from wild-type, PagP-expressing, or PagL-expressing *B. pertussis* strain Tohama and analysed by Tricine-SDS-PAGE. LPS isolated from the PagL$_{(Bb)}$-expressing strain appeared unaffected on the gel, whereas that from the PagP-expressing appeared potentially modified, since a band with a lower electrophoretic mobility than that of wild-type *B. pertussis* LPS was detected (FIG. 14). Furthermore, as compared to the PagP$_{(Bp)}$-expressing strain, the modification-efficiency appeared higher in the PagP$_{(Ec)}$-expressing strain (FIG. 14). To evaluate the possible LPS modifications in further detail, the lipid A moieties of the strains were analysed by ESI-MS in the negative-ion mode. This analysis revealed the presence of four major lipid A species in wild-type LPS (FIG. 15A). The peak at m/z 1557 represents the characteristic penta-acylated bis-phosphate species that is typically found in *B. pertussis* (Caroff et al., Microbes. Infect., 1994), whereas the peak at m/z 1477 corresponds to a penta-acylated mono-phosphate species. The two remaining peaks at m/z 1307 and 1251 represent deacylated lipid A species of the molecular ion at m/z 1477, which miss the primary 3-hydroxydecanoic acid residue at the 3 position or a primary 3-hydroxytetradecanoic acid residue (either at the 2 or the 3' position), respectively. These results indicate a high heterogeneity among the lipid A species in wild-type *B. pertussis*, which was apparently not resolved in the gel analysis (FIG. 14). Interestingly, calculation of the relative amounts of the individual lipid A species from the corresponding peak heights revealed that in wild-type *B. pertussis* LPS, a large quantity of lipid A species (~50%) consists of tetra-acylated forms. Furthermore, the large majority of lipid A species are mono-phosphate forms (~80%). To exclude the possibility that the high abundancy of under-acylated and hypo-phosphorylated lipid A species was an artefact of the hydrolysation procedure used to isolate lipid A, we tested whether shorter or longer periods of hydrolysation (varying between 1 and 4 h) influenced the relative abundance of the lipid A species, which was, however, not the case (data not shown). Furthermore, the total phosphate content of a solution with a known concentration of purified wild-type *B. pertussis* LPS was determined. Consistent with the high prevalence of mono-phosphate lipid A species detected by ESI-MS, only slightly more than half of the phosphate content expected, when LPS would have been fully phosphorylated, was detected (data not shown).

Upon expression of PagL$_{(Bb)}$ (FIG. 15B), three lipid A species, at m/z 1081, 1307, and 1387, respectively, were present. The major peak at m/z 1307 corresponds to the mono-phosphate deacylated form missing the 3-hydroxydecanoic acid residue at the 3 position, whereas the peak at m/z 1387 corresponds to the bis-phosphorylated form of the molecular ion at m/z 1307. The peak at m/z 1081 corresponds to a mono-phosphate form missing both a 3-hydroxydecanoic and a 3-hydroxytetradecanoic acid residue. The relative content of lipid A species that miss the 3-hydroxydecanoic acid residue at their 3 position was increased from about 37 percent in wild-type *B. pertussis* LPS to more than 92 percent in the strain expressing PagL$_{(Bb)}$. Thus, even though the electrophoretic mobility of the LPS was not affected (FIG. 14, lane 2), the pagL$_{(Bb)}$-encoded lipid A 3-O-deacylase was active in *B. pertussis*.

Upon expression of PagP$_{(Ec)}$ (FIG. 15C) and PagP$_{(Bp)}$ (FIG. 15D), several new lipid A species were detected (Table III). The peaks at m/z 1320, 1490, 1545, 1625, 1715, and 1796 correspond to the expected PagP-mediated palmitoylation of the molecular ions present at m/z 1081, 1251, 1307, 1387, 1477, and 1557, respectively. The difference in modification-efficiency between *E. coli* and *B. pertussis* PagP, which was seen after analysis by Tricine-SDS-PAGE (FIG. 14), was also revealed in the mass spectrometrical analysis. In the strain expressing *E. coli* PagP, ~47% of the total lipid A population was palmitoylated, in contrast to only ~9% in the strain expressing PagP$_{(Bp)}$. Interestingly, in the strain expressing PagP$_{(Bp)}$, in contrast to that expressing PagP$_{(EC)}$, lipid A species missing a 3-hydroxytetradecanoic acid residue were not found to be palmitoylated. A possible explanation for this discrepancy is the difference in specificity of the two PagP enzymes. Whereas *E. coli* PagP adds an acyl chain at the 2 position of lipid A, *B. pertussis* PagP adds a palmitate at the 3' position (Bishop et al., EMBO J., 2000; Preston et al., Mol. Microbiol., 2003). Thus, the complete absence of palmitoylated lipid A species that miss one 3-hydroxytetradecanoic acid residue in the strain expressing *B. pertussis* PagP suggests that the lipid A molecules missing a 3-hydroxytetradecanoic acid residue miss it specifically at their 3' position. This could then partially explain the difference in modification efficiency that was observed between the two PagP enzymes, as the substrate pool for *E. coli* PagP would be larger than that for *B. pertussis* PagP. Furthermore, this hypothesis is consistent with the presence of hypo-acylated lipid A species in vivo.

TABLE III

Relative abundance of lipid A molecular ions as determined by ESI-MS

| | 1081<br>−C14−3OH<br>−C10−3OH<br>−PO4 | 1251<br>−C14−3OH<br>−PO4 | 1307<br>−C10−3OH<br>−PO4 | 1320<br>−C14−3OH<br>−C10−3OH<br>−PO4<br>+C16 | 1331<br>−C14−3OH | 1387<br>−C10−3OH | 1477<br>−PO4 |
|---|---|---|---|---|---|---|---|
| Wild-type | 3.0 | 15.6 | 29.9 | 0.0 | 4.5 | 3.9 | 29.0 |
| PagL$_{(Bb)}$ | 8.5 | 2.1 | 70.9 | 0.0 | 0.0 | 12.8 | 3.5 |
| PagP$_{(Ec)}$ | 4.5 | 2.3 | 25.0 | 5.0 | 2.3 | 10.3 | 2.0 |
| PagP$_{(Bp)}$ | 8.3 | 5.0 | 27.6 | 0.0 | 6.1 | 21.3 | 3.0 |

| | 1490<br>−C14−3OH<br>−PO4<br>+C16 | 1545<br>−C10−3OH<br>−PO4<br>+C16 | 1557 | 1625<br>−C10−3OH<br>+C16 | 1715<br>−PO4<br>+C16 | 1796<br>+C16 | palmitoylate |
|---|---|---|---|---|---|---|---|
| Wild-type | 0.0 | 0.0 | 14.1 | 0.0 | 0.0 | 0.0 | 0.0 |
| PagL$_{(Bb)}$ | 0.0 | 0.0 | 2.1 | 0.0 | 0.0 | 0.0 | 0.0 |
| PagP$_{(Ec)}$ | 3.0 | 14.8 | 6.0 | 6.3 | 5.3 | 12.3 | 46.5 |
| PagP$_{(Bp)}$ | 0.0 | 3.9 | 17.1 | 2.5 | 0.0 | 2.9 | 9.1 |

REFERENCES

1. Raetz, C. R. H., and Whitfield, C. (2002) *Annu. Rev. Biochem.* 71, 635-700
2. Loppnow, H., Brade, H., Durrbaum, I., Dinarello, C. A., Kusumoto, S., Rietschel, E. T., and Flad, H. D. (1989) *J. Immunol.* 142, 3229-3238
3. Steeghs, L., Bems, M., ten Hove, J., de Jong, A., Roholl, P., van Alphen, L., Tommassen, J., and van der Ley, P. (2002) *Cell. Microbiol.* 4, 599-611
4. Nikaido, H., and Vaara, M. (1987) in *Escherichia coli and Salmonella: Cellular and Molecular Biology* (Neidhardt, F. C., ed) Vol. 1, pp. 7-22, American Society for Microbiology, Washington, D.C.
5. Caroff, M., Karibian, D., Cavaillon, J-M., and Haeffner-Cavaillon, N. (2002) *Microbes Infect.* 4, 915-926
6. Guo, L., Lim, K. B., Gunn, J. S., Bainbridge, B., Darveau, R. P., Hackett, M., and Miller, S. I. (1997) *Science* 276, 250-253
7. Guo, L., Lim, K. B., Poduje, C. M., Daniel, M., Gunn, J. S., Hackett, M., and Miller, S. I. (1998) *Cell* 95, 189-198
8. Gunn, J. S., Belden, W. J., Miller, S. I. (1998) *Microb. Pathog.* 25, 77-90
9. Gunn, J. S., Lim, K. B., Krueger, J., Kim, K., Guo, L., Hackett, M., and Miller, S. I. (1998) *Mol. Microbiol.* 27, 1171-1182
10. Gunn, J. S., Ryan, S. S., Van Velkinburgh, J. C., Ernst, R. K., and Miller, S. I. (2000) *Infect. Immun.* 68, 6139-6146
11. Miller, S. I., Kukral, A. M., and Mekalanos, J. J. (1989) *Proc. Natl. Acad. Sci. U.S.A.* 86, 5054-5058
12. Gunn, J. S., and Miller, S. I. (1996) *J. Bacteriol.* 178, 6857-6864
13. Ernst, R. K., Guina, T., and Miller, S. I. (1999) *J. Infect. Dis.* 179, Suppl. 2, 326-330
14. Ernst, R. K., Yi, E. C., Guo, L., Lim, K. B., Burns, J. L., Hackett, M., and Miller, S. I. (1999) *Science* 286, 1561-1565
15. Trent, M. S., Ribeiro, A. A., Lin, S., Cotter, R. J., and Raetz, C. R. H. (2001) *J. Biol. Chem.* 276, 43122-43131
16. Lee, H., Hsu, F. F., Turk, J., and Groisman, E. A. (2004) *J. Bacteriol.* 186, 4124-4133
17. Gibbons, H. S., Lin, S., Cotter, R. J., and Raetz C. R. H. (2000) *J. Biol. Chem.* 275, 32940-32949
18. Karbarz, M. J., Kalb, S. R., Coffer, R. J., and Raetz, C. R. H. (2003) *J. Biol. Chem.* 278, 39269-39279
19. Bishop, R. E., Gibbons, H. S., Guina, T., Trent, M. S., Miller, S. I., and Raetz, C. R. H. (2000) *EMBO J.* 19, 5071-5080
20. Tanamoto, K., and Azumi, S. (2000) *J. Immunol.* 164, 3149-3156
21. Robey, M., O'Connell, W., and Cianciotto, N. P. (2001) *Infect. Immun.* 69, 4276-4286
22. Trent, M. S., Pabich, W., Raetz, C. R. H., and Miller, S. I. (2001) *J. Biol. Chem.* 276, 9083-9092
23. Bhat, U. R., Forsberg, L. S., and Carlson, R. W. (1994) *J. Biol. Chem.* 269, 14402-14410
24. Moran, A. P., Lindner, B., and Walsh, E. J. (1997) *J. Bacteriol.* 179, 6453-6463
25. Kumada, H., Haishima, Y., Umemoto, T., and Tanamoto, K. (1995) *J. Bacteriol.* 177, 2098-2106
26. Tommassen, J., van Tol, H., and Lugtenberg, B. (1983) *EMBO J.* 2, 1275-1279

27. Sambrook, J., Fritsch, E. F., and Maniatis, T. (1989) in *Molecular Cloning: A Laboratory Manual*. Cold Spring Harbour Laboratory Press, Cold Spring Harbour (N.Y.)
28. Laemmli, U. K. (1970) *Nature* 227, 680-685
29. Dekker, N., Merck, K., Tommassen, J., and Verheij, H. M. (1995) *Eur. J. Biochem.* 232, 214-219
30. Lesse, A. J., Campagnari, A. A., Bittner, W. E., and Apicella, M. A. (1990) *J. Immunol. Methods* 126, 109-117
31. Tsai, C. M., and Frasch, C. E. (1982) *Anal. Biochem.* 119, 115-119
32. Westphal, O., and Jann, J. K. (1965) *Methods Carbohydr. Chem.* 5, 83-91
33. Wilm, M., and Mann, M. (1996) *Anal. Chem.* 68, 1-8
34. Altschul, S. F., Gish, W., Miller, W., Myers, E. W., and Lipman, D. J. (1990) *J. Mol. Biol.* 215, 403-410
35. Nielsen, H., Brunak, S., and von Heijne, G. (1999) *Protein Eng.* 12, 3-9
36. Parkhill, J., Sebaihia, M., Preston, A., Murphy, L. D., Thomson, N., Harris, D. E., Holden, M. T., Churcher, C. M., Bentley, S. D., Mungall, K. L., Cerdeno-Tarraga, A. M., Temple, L., James, K., Harris, B., Quail, M. A., Achtman, M., Atkin, R., Baker, S., Basham, D., Bason, N., Cherevach, I., Chillingworth, T., Collins, M., Cronin, A., Davis, P., Doggett, J., Feltwell, T., Goble, A., Hamlin, N., Hauser, H., Holroyd, S., Jagels, K., Leather, S., Moule, S., Norberczak, H., O'Neil, S., Ormond, D., Price, C., Rabbinowitsch, E., Rutter, S., Sanders, M., Saunders, D., Seeger, K., Sharp, S., Simmonds, M., Skelton, J., Squares, R., Squares, S., Stevens, K., Unwin, L., Whitehead, S., Barrell, B. G., and Maskell, D. J. (2003) *Nat. Genet.* 35, 32-40
37. Snijder, H. J., Ubarretxena-Belandia, I., Blaauw, M., Kalk, K. H., Verheij, H. M., Egmond, M. R., Dekker, N., and Dijkstra, B. W. (1999) *Nature* 401, 717-721
38. McClelland, M., Sanderson, K. E., Spieth, J., Clifton, S. W., Latreille, P., Courtney, L., Porwollik, S., Ali, J., Dante, M., Du, F., Hou, S., Layman, D., Leonard, S., Nguyen, C., Scott, K., Holmes, A., Grewal, N., Mulvaney, E., Ryan, E., Sun, H., Florea, L., Miller, W., Stoneking, T., Nhan, M., Waterston, R., and Wilson, R. K. (2001) *Nature* 413, 852-856
39. Basu, S. S., White, K. A., Que, N. L., and Raetz, C. R. H. (1999) *J. Biol. Chem.* 274, 11150-11158
40. Kulshin, V. A., Zahringer, U., Lindner, B., Jager, K. E., Dmitriev, B. A., and Rietschel, E. T. (1991) *Eur. J. Biochem.* 198, 697-704
41. Hwang, P. M., Choy, W. Y., Lo, E. I., Chen, L., Forman-Kay, J. D., Raetz, C. R., Prive, G. G., Bishop, R. E., and Kay, L. E. (2002) *Proc. Natl. Acad. Sci. USA.* 99, 13560-13565
42. Kol, M. A., van Dalen, A., de Kroon, A. I., and de Kruijff, B. (2003) *J. Biol. Chem.* 278, 24586-24593
43. von Heijne, G. (1983) *Eur. J Biochem.* 133, 17-21
44. Tommassen, J. (1988) in *Membrane Biogenesis* (Op den Kamp, J. A. F., ed) NATO ASI series, Vol. H16, pp. 351-373. Springer Verlag, Berlin, Heidelberg, New York.
45. Haas, D., and Holloway, B. W. (1976) *Mol. Gen. Genet.* 144, 243-251
46. Pace, J., Hayman, M. J., and Galan, J. E. (1993) *Cell* 72, 505-514
47. Hanahan, D. (1983) *J. Mol. Biol.* 166, 557-580
48. Thalen, M., van den IJssel, J., Jiskoot, W., Zomer, B., Roholl, P., de Gooijer, C., Beuvery, C., and Trampen, J. (1999) *J. Biotechnol.* 75, 147-159.
49. Ziegler-Heitbrock, H. W., Thiel, E., Futterer, A., Herzog, V., Wirtz, A., and Riethmuller, G. (1988) *J. Cancer* 41, 456-461
50. Simon, R., Priefer, U., and Puhler, A. A. (1983) *Bio/Technol.* 1, 784-791
51. Furste, J. P., Pansegrau, W., Frank, R., Blocker, H., Scholz, P., Bagdasarian, M., and Lanka, E. (1986) *Gene* 48, 119-131
52. Stibitz, S., Black, W., and Falkow, S. (1986) *Gene* 50, 133-140

---

The invention claimed is:

1. A Gram negative bacterium comprising an expression vector that comprises a nucleic acid sequence encoding a polypeptide with lipid A 3-O-deacylase activity, wherein the polypeptide has at least 95% amino acid sequence identity with SEQ ID NO: 1, wherein expression of the nucleic acid sequence increases lipid A 3-O-deacylase activity in said bacterium.

2. The bacterium according to claim 1 which is selected from the group consisting of the following species:
   (a) *Bordetella pertussis*, or
   (b) *Bordetella parapertussis*, or
   (c) *Bordetella bronchiseptica*, or
   (d) a *Neisseria* species.

3. The bacterium according to claim 2 which is a member of the *Bordetella pertussis* species.

4. The bacterium according to claim 2, wherein the *Neisseria* species is selected from the group consisting of *N. meningitidis, N. gonorrhoeae* and *N. lactamica.*

5. The bacterium according to claim 1 comprising a partially or fully 3-O-deacylated lipopolysaccharide (LPS) species in its outer membrane.

6. The bacterium according to claim 5 wherein the LPS is palmitoylated.

7. The bacterium according to claim 6 which is a member of the *Bordetella pertussis* species.

8. The bacterium according to claim 1 wherein the nucleic acid sequence encodes a polypeptide the sequence of which is SEQ ID NO:1.

9. The bacterium according to claim 8 which is selected from the group consisting of the following species:

(a) *Bordetella pertussis*, or (b) *Bordetella parapertussis*, or (c) *Bordetella bronchiseptica*, or (d) a *Neisseria* species.

10. The bacterium according to claim 9 which is a member of the *Bordetella pertussis* species.

11. The bacterium according to claim 9, wherein the *Neisseria* species is selected from the group consisting of *N. meningitidis, N. gonorrhoeae* and *N. lactamica.*

12. The bacterium according to claim 9 comprising a partially or fully 3-O-deacylated lipopolysaccharide (LPS) species in its outer membrane.

13. The bacterium according to claim 12 which is a member of the *Bordetella pertussis* species.

14. The bacterium according to claim 12 wherein the LPS is palmitoylated.

15. The bacterium according to claim 14 which is a member of the *Bordetella pertussis* species.

16. A whole cell vaccine comprising the bacterium according to claim 1 and a pharmaceutically acceptable excipient or carrier.

17. A whole cell vaccine comprising the bacterium according to claim 2 and a pharmaceutically acceptable excipient or carrier.

18. A whole cell vaccine comprising the bacterium according to claim 3 and a pharmaceutically acceptable excipient or carrier.

19. A whole cell vaccine comprising the bacterium according to claim 4 and a pharmaceutically acceptable excipient or carrier.

20. A whole cell vaccine comprising the bacterium according to claim 5 and a pharmaceutically acceptable excipient or carrier.

21. A whole cell vaccine comprising the bacterium according to claim 6 and a pharmaceutically acceptable excipient or carrier.

22. A whole cell vaccine comprising the bacterium according to claim 7 and a pharmaceutically acceptable excipient or carrier.

23. A whole cell vaccine comprising the bacterium according to claim 8 and a pharmaceutically acceptable excipient or carrier.

24. A whole cell vaccine comprising the bacterium according to claim 9 and a pharmaceutically acceptable excipient or carrier.

25. A whole cell vaccine comprising the bacterium according to claim 10 and a pharmaceutically acceptable excipient or carrier.

26. A whole cell vaccine comprising the bacterium according to claim 11 and a pharmaceutically acceptable excipient or carrier.

27. A whole cell vaccine comprising the bacterium according to claim 12 and a pharmaceutically acceptable excipient or carrier.

28. A whole cell vaccine comprising the bacterium according to claim 13 and a pharmaceutically acceptable excipient or carrier.

29. A whole cell vaccine comprising the bacterium according to claim 14 and a pharmaceutically acceptable excipient or carrier.

30. A whole cell vaccine comprising the bacterium according to claim 15 and a pharmaceutically acceptable excipient or carrier.

31. A method for treating or preventing a *Bordetella* infection in a subject, comprising, administering to a subject in need thereof bacteria according to claim 2, wherein the bacteria are one of said *Bordetella* species.

32. A method for eliciting an immune response against *Bordetella* bacteria in a subject, comprising administering to the subject the vaccine according to claim 17, wherein the bacterium is one of said *Bordetella* species.

* * * * *